(12) United States Patent
Valentine et al.

(10) Patent No.: US 12,172,121 B2
(45) Date of Patent: Dec. 24, 2024

(54) SYSTEM AND METHOD FOR CONCENTRATING GAS

(71) Applicant: INVACARE CORPORATION, Elyria, OH (US)

(72) Inventors: Alex P. Valentine, North Olmsted, OH (US); William A. Null, Nova, OH (US); Matthew E. Monaghan, Chagrin Falls, OH (US)

(73) Assignee: VENTEC LIFE SYSTEMS, INC., Dublin, OH (US)

( * ) Notice: Subject to any disclaimer, the term of this patent is extended or adjusted under 35 U.S.C. 154(b) by 182 days.

(21) Appl. No.: 17/376,266

(22) Filed: Jul. 15, 2021

(65) Prior Publication Data

US 2022/0016563 A1    Jan. 20, 2022

Related U.S. Application Data

(60) Provisional application No. 63/052,700, filed on Jul. 16, 2020.

(51) Int. Cl.
*B01D 53/04* (2006.01)
*A61M 16/00* (2006.01)
*A61M 16/10* (2006.01)

(52) U.S. Cl.
CPC ......... *B01D 53/04* (2013.01); *A61M 16/0063* (2014.02); *A61M 16/101* (2014.02);
(Continued)

(58) Field of Classification Search
CPC ............ A61M 16/0063; A61M 16/101; A61M 16/105; B01D 53/04; B01D 53/047
See application file for complete search history.

(56) References Cited

U.S. PATENT DOCUMENTS

| 3,494,296 A | 2/1970 | Gluntz |
| 3,602,527 A | 8/1971 | Goetz |

(Continued)

FOREIGN PATENT DOCUMENTS

| AU | 1999015998 A | 8/1999 |
| AU | 200072682 A1 | 5/2001 |

(Continued)

OTHER PUBLICATIONS

US 6,979,301 B2, 12/2005, Van Brunt et al. (withdrawn)
(Continued)

*Primary Examiner* — Sharon Pregler
(74) *Attorney, Agent, or Firm* — Calfee, Halter & Griswold LLP

(57) ABSTRACT

Gas concentrating systems and methods are provided. In one embodiment, a gas concentrating system and method is provided that includes component heat management. The heat management system can include, for example, one or more air cooling paths. The air cooling paths direct cooling air into and out of component spaces having heat-generating mechanisms. In other embodiments, the heat management system can also include component spaces that are insulated against the heat of heat-generating components. By cooling heat-generating components and insulating other components from heat, reduced wear and extended component life can be achieved. This reduces component failure and costly service to repair or replace failed or worn components. Also, gas concentrating systems and methods are provided for mounting system components with or without the use fasteners and in combination with or without component heat management.

17 Claims, 17 Drawing Sheets

(52) U.S. Cl.
CPC ... *A61M 16/105* (2013.01); *A61M 2205/3606* (2013.01); *A61M 2205/362* (2013.01); *B01D 2253/116* (2013.01); *B01D 2256/12* (2013.01); *B01D 2257/102* (2013.01); *B01D 2259/4533* (2013.01); *B01D 2259/4541* (2013.01)

(56) References Cited

U.S. PATENT DOCUMENTS

| | | |
|---|---|---|
| 3,608,833 A | 9/1971 | Hankins |
| 4,127,395 A | 11/1978 | McKey et al. |
| 4,144,037 A | 3/1979 | Armond et al. |
| 4,247,311 A | 1/1981 | Seibert |
| 4,378,982 A | 4/1983 | Mcombs |
| 4,449,990 A | 5/1984 | Tedford |
| 4,454,596 A | 6/1984 | Wunsch et al. |
| 4,561,287 A | 12/1985 | Rowland |
| 4,575,042 A | 3/1986 | Grimland |
| 4,648,888 A | 3/1987 | Rowland |
| 4,826,510 A | 5/1989 | McCombs |
| 4,832,711 A | 5/1989 | Christel, Jr. et al. |
| 4,932,402 A | 6/1990 | Snook et al. |
| 4,971,609 A | 11/1990 | Pawlos |
| 5,057,822 A | 10/1991 | Hoffman |
| 5,099,837 A | 3/1992 | Russel et al. |
| 5,101,656 A | 4/1992 | Miller |
| 5,144,945 A | 8/1992 | Nishino et al. |
| 5,258,056 A | 11/1993 | Shirley et al. |
| 5,294,049 A | 3/1994 | Trunkle et al. |
| 5,298,226 A | 3/1994 | Nowobilski |
| 5,469,372 A | 11/1995 | McBrearty et al. |
| 5,474,595 A | 12/1995 | McCombs |
| 5,538,544 A | 7/1996 | Nowobilski |
| 5,593,478 A | 1/1997 | Hill et al. |
| 5,626,131 A | 5/1997 | Chua et al. |
| 5,680,409 A | 10/1997 | Qin et al. |
| 5,720,276 A | 2/1998 | Kobatake et al. |
| 5,779,773 A | 7/1998 | Cam et al. |
| 5,785,681 A | 7/1998 | Indravudh |
| 5,906,672 A | 5/1999 | Michaels et al. |
| 5,917,135 A | 6/1999 | Michaels et al. |
| 5,931,160 A | 8/1999 | Gilmore et al. |
| 5,983,416 A | 11/1999 | Idland |
| 5,988,165 A | 11/1999 | Richey, II et al. |
| 6,022,634 A | 2/2000 | Ramunni |
| 6,051,051 A | 4/2000 | Hees et al. |
| 6,106,245 A | 8/2000 | Cabuz |
| 6,139,426 A | 10/2000 | Koerber |
| 6,151,586 A | 11/2000 | Brown |
| 6,152,134 A | 11/2000 | Webber et al. |
| 6,266,995 B1 | 7/2001 | Scott |
| 6,279,377 B1 | 8/2001 | Cao |
| 6,427,690 B1 | 8/2002 | McCombs et al. |
| 6,442,433 B1 | 8/2002 | Linberg |
| 6,472,988 B1 | 10/2002 | Feld et al. |
| 6,517,610 B1 | 2/2003 | La Houssaye |
| 6,520,176 B1 | 2/2003 | Dubois et al. |
| 6,561,187 B2 | 5/2003 | Schmidt et al. |
| 6,629,525 B2 | 10/2003 | Hill et al. |
| 6,651,658 B1 | 11/2003 | Hill et al. |
| 6,691,702 B2 | 2/2004 | Appel et al. |
| 6,764,534 B2 | 7/2004 | McCombs et al. |
| 6,837,244 B2 | 1/2005 | Yagi et al. |
| 6,878,186 B2 | 4/2005 | Neary |
| 6,949,133 B2 | 9/2005 | McCombs et al. |
| 6,962,654 B2 | 11/2005 | Arnaud |
| 7,036,729 B2 | 5/2006 | Chung |
| 7,115,104 B2 | 10/2006 | Van Brunt et al. |
| 7,278,983 B2 | 10/2007 | Ireland et al. |
| 7,294,170 B2 | 11/2007 | Richey, II et al. |
| 7,306,657 B2 | 12/2007 | Yagi et al. |
| 7,329,304 B2 | 2/2008 | Bliss et al. |
| 7,331,340 B2 | 2/2008 | Barney |
| 7,393,382 B2 | 7/2008 | Givens |
| 7,425,203 B2 | 9/2008 | Van Brunt et al. |
| 7,431,032 B2 | 10/2008 | Jagger et al. |
| 7,445,663 B1 | 11/2008 | Hunter et al. |
| 7,455,717 B2 | 11/2008 | Sprinkle |
| 7,491,182 B2 | 2/2009 | Van Brunt |
| 7,505,374 B2 | 3/2009 | Booty, Jr. et al. |
| 7,552,731 B2 | 6/2009 | Jorczak et al. |
| 7,604,004 B2 | 10/2009 | Jagger et al. |
| 7,604,005 B2 | 10/2009 | Jagger et al. |
| 7,652,571 B2 | 1/2010 | Parkulo et al. |
| 7,662,638 B2 | 2/2010 | Dadala et al. |
| 7,686,870 B1 | 3/2010 | Deane et al. |
| 7,722,698 B2 | 5/2010 | Thompson et al. |
| 7,722,700 B2 | 5/2010 | Sprinkle |
| 7,753,996 B1 * | 7/2010 | Deane ................. A61M 16/101 128/205.24 |
| 7,766,010 B2 | 8/2010 | Jagger et al. |
| 7,794,522 B2 * | 9/2010 | Bliss ................... B01D 53/053 128/205.24 |
| 7,826,728 B2 | 11/2010 | Konno et al. |
| 7,866,315 B2 | 1/2011 | Jagger et al. |
| 7,875,105 B2 | 1/2011 | Chambers et al. |
| 7,922,789 B1 | 4/2011 | Deane et al. |
| 7,931,197 B2 | 4/2011 | Brandt et al. |
| 8,013,739 B2 | 9/2011 | Parkulo et al. |
| 8,062,003 B2 | 11/2011 | Goertzen et al. |
| 8,070,853 B2 | 12/2011 | Sprinkle |
| 8,092,396 B2 | 1/2012 | Bagha et al. |
| 8,231,541 B2 | 7/2012 | Colquitt et al. |
| 8,262,771 B2 | 9/2012 | Seki et al. |
| 8,366,402 B2 | 2/2013 | St. Michel |
| 8,366,815 B2 | 2/2013 | Taylor et al. |
| 8,377,181 B2 | 2/2013 | Taylor et al. |
| 8,421,465 B2 | 4/2013 | Carter |
| 8,547,062 B2 | 10/2013 | Carter et al. |
| 8,568,519 B2 | 10/2013 | Taylor et al. |
| 8,599,016 B2 | 12/2013 | Parkulo et al. |
| 8,668,767 B2 | 3/2014 | Sprinkle et al. |
| 8,677,998 B2 | 3/2014 | Yamaura et al. |
| 8,726,744 B2 | 5/2014 | Alburty et al. |
| 8,818,824 B2 | 8/2014 | DeBusk et al. |
| 8,956,289 B2 | 2/2015 | Kitajima et al. |
| 9,058,741 B2 | 6/2015 | Steinhauer et al. |
| 9,072,849 B2 | 7/2015 | Steinhauer et al. |
| 9,132,377 B2 | 9/2015 | Richey, II et al. |
| 9,266,053 B2 | 2/2016 | Shelnutt et al. |
| 9,317,660 B2 | 4/2016 | Burich et al. |
| 9,327,090 B2 | 5/2016 | Steinhauer et al. |
| 9,352,110 B2 | 5/2016 | Steinhauer et al. |
| 9,364,626 B2 | 6/2016 | Carter et al. |
| 9,440,179 B2 | 9/2016 | Wilkinson et al. |
| 9,460,262 B2 | 10/2016 | Kaufman et al. |
| 9,462,977 B2 | 10/2016 | Horseman |
| 9,637,280 B2 | 5/2017 | Gotoh |
| 9,693,734 B2 | 7/2017 | Horseman |
| 9,714,860 B2 | 7/2017 | Obenchain |
| 9,763,585 B2 | 9/2017 | Addison et al. |
| 9,782,557 B2 | 10/2017 | Wilkinson et al. |
| 9,788,735 B2 | 10/2017 | Ai-Ali |
| 9,808,156 B2 | 11/2017 | Horseman |
| 9,833,142 B2 | 12/2017 | Horseman |
| 9,838,508 B2 | 12/2017 | Salem |
| 9,839,786 B2 | 12/2017 | Rondoni et al. |
| 9,872,623 B2 | 1/2018 | Ai-Ali |
| 9,872,965 B2 | 1/2018 | Baloa et al. |
| 9,956,370 B2 | 5/2018 | Wilkinson et al. |
| 9,957,125 B2 | 5/2018 | Ray |
| 9,990,466 B2 | 6/2018 | DeBusk et al. |
| 10,004,435 B2 | 6/2018 | Larvenz et al. |
| 10,010,969 B2 | 7/2018 | Reed et al. |
| 10,037,044 B2 | 7/2018 | Laberge et al. |
| 10,058,269 B2 | 8/2018 | Lynn |
| 10,108,785 B2 | 10/2018 | Kamen et al. |
| 10,139,282 B2 | 11/2018 | Chrostowski |
| 10,148,912 B1 | 12/2018 | Oliver et al. |
| 10,179,217 B2 | 1/2019 | Steinhauer et al. |
| 10,252,037 B2 | 4/2019 | Degen et al. |
| 10,271,779 B2 | 4/2019 | Addison et al. |
| 10,349,901 B2 | 7/2019 | Osypka et al. |
| 10,357,628 B2 | 7/2019 | Jagger et al. |
| 10,391,019 B2 | 8/2019 | Stryker et al. |

(56) References Cited

U.S. PATENT DOCUMENTS

| | | |
|---|---|---|
| 10,426,904 B2 | 10/2019 | Broborg et al. |
| 10,496,788 B2 | 12/2019 | Amarasingham et al. |
| 10,521,720 B2 | 12/2019 | Detzler et al. |
| 10,592,637 B2 | 3/2020 | Velamuri et al. |
| 10,630,814 B2 | 4/2020 | Barnes et al. |
| 10,753,598 B2 | 8/2020 | Chien |
| 10,948,175 B2 | 3/2021 | Chien |
| 2002/0053286 A1 | 5/2002 | Czabala |
| 2002/0096174 A1 | 7/2002 | Hill et al. |
| 2003/0068828 A1 | 4/2003 | Dadala et al. |
| 2003/0180164 A1 | 9/2003 | Bunner et al. |
| 2003/0215342 A1 | 11/2003 | Higashino |
| 2003/0231967 A1 | 12/2003 | Najafi et al. |
| 2004/0079359 A1 | 4/2004 | Aylsworth et al. |
| 2004/0167464 A1 | 8/2004 | Ireland et al. |
| 2004/0237488 A1 | 12/2004 | Stenersen |
| 2005/0259088 A1 | 11/2005 | Ogasawara et al. |
| 2005/0263199 A1 | 12/2005 | Meheen |
| 2006/0005842 A1 | 1/2006 | Rashad |
| 2006/0025932 A1 | 2/2006 | Dadala et al. |
| 2006/0086251 A1 | 4/2006 | Sprinkle |
| 2006/0092768 A1 | 5/2006 | Demas |
| 2006/0092769 A1 | 5/2006 | Demas |
| 2006/0174871 A1 | 8/2006 | Jagger et al. |
| 2006/0174872 A1 | 8/2006 | Jagger |
| 2006/0219245 A1 | 10/2006 | Holder |
| 2006/0220881 A1 | 10/2006 | Al et al. |
| 2006/0227123 A1 | 10/2006 | Bychkov et al. |
| 2006/0230768 A1 | 10/2006 | Huber et al. |
| 2006/0230929 A1 | 10/2006 | Bliss et al. |
| 2006/0251408 A1 | 11/2006 | Konno et al. |
| 2007/0034590 A1 | 2/2007 | Hidding |
| 2007/0056584 A1 | 3/2007 | Jagger et al. |
| 2007/0140869 A1 | 6/2007 | St. Michel |
| 2007/0144519 A1 | 6/2007 | Henry et al. |
| 2007/0250017 A1 | 10/2007 | Carred et al. |
| 2008/0007396 A1 | 1/2008 | Parkulo et al. |
| 2008/0066616 A1 | 3/2008 | Sprinkle |
| 2008/0136652 A1 | 6/2008 | Vaisnys et al. |
| 2008/0165629 A1 | 7/2008 | Billeaudeaux |
| 2008/0238323 A1 | 10/2008 | Chan et al. |
| 2008/0246277 A1 | 10/2008 | Gallagher et al. |
| 2008/0257145 A1 | 10/2008 | Sprinkle |
| 2008/0262657 A1 | 10/2008 | Howell et al. |
| 2008/0294348 A1 | 11/2008 | Tanaka et al. |
| 2009/0065526 A1 | 3/2009 | Sprinkle |
| 2009/0118632 A1 | 5/2009 | Goepp |
| 2009/0126736 A1 | 5/2009 | Taylor et al. |
| 2009/0209839 A1 | 8/2009 | Ochs et al. |
| 2009/0211438 A1 | 8/2009 | Thompson et al. |
| 2009/0211448 A1 | 8/2009 | McClain |
| 2009/0216747 A1 | 8/2009 | Li et al. |
| 2009/0232706 A1 | 9/2009 | Dadala et al. |
| 2009/0316533 A1 | 12/2009 | Liu |
| 2010/0024729 A1 | 2/2010 | Cao |
| 2010/0071698 A1 | 3/2010 | Kiritake |
| 2010/0095841 A1 | 4/2010 | Naheiri |
| 2010/0106458 A1 | 4/2010 | Leu |
| 2010/0114218 A1 | 5/2010 | Heath |
| 2010/0146426 A1 | 6/2010 | Parkulo et al. |
| 2010/0214877 A1 | 8/2010 | Turk |
| 2010/0242734 A1 | 9/2010 | Maeda et al. |
| 2010/0253505 A1 | 10/2010 | Chou |
| 2010/0294127 A1 | 11/2010 | Dolensky |
| 2011/0017216 A1 | 1/2011 | Van Brunt et al. |
| 2011/0056904 A1 | 3/2011 | Rozenberg |
| 2011/0073107 A1 | 3/2011 | Rodman et al. |
| 2011/0080348 A1 | 4/2011 | Lin et al. |
| 2011/0126829 A1 | 6/2011 | Carter |
| 2011/0128008 A1 | 6/2011 | Carter |
| 2011/0148773 A1 | 6/2011 | Rudolph |
| 2011/0148775 A1 | 6/2011 | Rudolph et al. |
| 2011/0211425 A1 | 9/2011 | Liu |
| 2011/0260850 A1 | 10/2011 | Ringenwald |
| 2011/0315140 A1 | 12/2011 | Shuman |
| 2012/0036461 A1 | 2/2012 | Parkulo et al. |
| 2012/0122545 A1 | 5/2012 | Watkins et al. |
| 2012/0321529 A1 | 12/2012 | Guo |
| 2013/0012788 A1 | 1/2013 | Horseman |
| 2013/0012789 A1 | 1/2013 | Horseman |
| 2013/0012790 A1 | 1/2013 | Horseman |
| 2013/0193100 A1 | 8/2013 | Lamoureux |
| 2013/0233168 A1 | 9/2013 | Richey, II |
| 2013/0264218 A1 | 10/2013 | Vinton et al. |
| 2013/0297330 A1 | 11/2013 | Kamen et al. |
| 2013/0333702 A1 | 12/2013 | Baloa et al. |
| 2014/0000604 A1 | 1/2014 | Steinhauer et al. |
| 2014/0000605 A1 | 1/2014 | Steinhauer et al. |
| 2014/0000607 A1 | 1/2014 | Steinhauer et al. |
| 2014/0000608 A1 | 1/2014 | Steinhauer et al. |
| 2014/0000609 A1 | 1/2014 | Steinhauer et al. |
| 2014/0002246 A1 | 1/2014 | Steinhauer et al. |
| 2014/0006041 A1 | 1/2014 | Steinhauer et al. |
| 2014/0006052 A1 | 1/2014 | Steinhauer et al. |
| 2014/0007405 A1 | 1/2014 | Chambers et al. |
| 2014/0049792 A1 | 2/2014 | Ha |
| 2014/0163335 A1 | 6/2014 | Horseman |
| 2014/0163336 A1 | 6/2014 | Horseman |
| 2014/0163337 A1 | 6/2014 | Horseman |
| 2014/0166003 A1 | 6/2014 | Van Brunt et al. |
| 2014/0188516 A1 | 7/2014 | Kamen et al. |
| 2014/0190348 A1 | 7/2014 | Richey, II et al. |
| 2014/0343854 A1 | 11/2014 | Wollard |
| 2015/0077245 A1 | 3/2015 | Kaufman et al. |
| 2015/0128800 A1 | 5/2015 | Bliss et al. |
| 2015/0164390 A1 | 6/2015 | Larvenz et al. |
| 2015/0174359 A1 | 6/2015 | Elliott et al. |
| 2015/0213224 A1 | 7/2015 | Amarasingham et al. |
| 2015/0234993 A1 | 8/2015 | Detzler et al. |
| 2015/0238721 A1 | 8/2015 | Rumph |
| 2015/0250960 A1 | 9/2015 | Broborg et al. |
| 2015/0362929 A1 | 12/2015 | Laberge et al. |
| 2016/0022971 A1 | 1/2016 | Degen et al. |
| 2016/0152430 A1 | 6/2016 | Ray |
| 2016/0189345 A1 | 6/2016 | Fujita et al. |
| 2016/0206838 A1 | 7/2016 | Steinhauer et al. |
| 2016/0275261 A1 | 9/2016 | Velamuri et al. |
| 2016/0303388 A1 | 10/2016 | Rondoni |
| 2016/0324425 A1 | 11/2016 | Addison et al. |
| 2016/0367197 A1 | 12/2016 | Addison et al. |
| 2016/0371479 A1 | 12/2016 | Wynen et al. |
| 2016/0375218 A1 | 12/2016 | Sprinkle et al. |
| 2016/0378067 A1 | 12/2016 | Bishop |
| 2017/0000395 A1 | 1/2017 | Addison et al. |
| 2017/0000423 A1 | 1/2017 | Addison et al. |
| 2017/0011131 A1 | 1/2017 | Li et al. |
| 2017/0017767 A1 | 1/2017 | Flower et al. |
| 2017/0053077 A1 | 2/2017 | Osypka et al. |
| 2017/0063456 A1 | 3/2017 | Yamasaki et al. |
| 2017/0080262 A1 | 3/2017 | Freres et al. |
| 2017/0117444 A1 | 4/2017 | Stoll et al. |
| 2017/0119235 A1 | 5/2017 | Hyde et al. |
| 2017/0202728 A1 | 7/2017 | Stryker |
| 2017/0221414 A1 | 8/2017 | Endo |
| 2017/0224231 A1 | 8/2017 | Ai-Ali |
| 2017/0224233 A1 | 8/2017 | Ai-Ali |
| 2017/0291708 A1 | 10/2017 | Buenting et al. |
| 2018/0014791 A1 | 1/2018 | Montgomery et al. |
| 2018/0156667 A1 | 6/2018 | Chrostowski |
| 2018/0192965 A1 | 7/2018 | Rose et al. |
| 2018/0271421 A1 | 9/2018 | Larvenz et al. |
| 2018/0279475 A1 | 9/2018 | Kloth et al. |
| 2018/0314416 A1 | 11/2018 | Powderly et al. |
| 2018/0369532 A1 | 12/2018 | Nebrigic |
| 2019/0065973 A1 | 2/2019 | Elwakeel |
| 2019/0068760 A1 | 2/2019 | Barnes et al. |
| 2019/0134340 A1 | 5/2019 | Nebrigac |
| 2019/0143056 A1 | 5/2019 | Steinhauer et al. |
| 2019/0200577 A1 | 7/2019 | Kath |
| 2019/0295718 A1 | 9/2019 | Lawhorn |
| 2019/0341793 A1 | 11/2019 | Chien |
| 2019/0374139 A1 | 12/2019 | Kiani et al. |
| 2020/0013501 A1 | 1/2020 | Page |
| 2020/0016605 A1 | 1/2020 | Nebrigac |

(56) References Cited

U.S. PATENT DOCUMENTS

| | | | |
|---|---|---|---|
| 2020/0035348 A1 | 1/2020 | Sartor et al. |
| 2020/0060545 A1 | 2/2020 | Maher et al. |
| 2020/0064011 A1 | 2/2020 | Nakano |
| 2020/0081856 A1 | 3/2020 | Kojima |
| 2020/0146442 A1 | 5/2020 | Rutzke |
| 2020/0264031 A1 | 8/2020 | Lease et al. |
| 2021/0252317 A1 | 8/2021 | Peake |
| 2021/0366320 A1 | 11/2021 | Wang et al. |
| 2022/0305428 A1 | 9/2022 | Yehya |

FOREIGN PATENT DOCUMENTS

| | | |
|---|---|---|
| AU | 748829 B2 | 6/2002 |
| AU | 200072387 A | 6/2002 |
| AU | 2008240038 A1 | 10/2009 |
| AU | 2010282150 A1 | 7/2012 |
| AU | 2012279039 A1 | 1/2014 |
| AU | 2012279044 A1 | 1/2014 |
| AU | 2012279110 A1 | 1/2014 |
| AU | 2013364131 A1 | 7/2015 |
| AU | 2013364131 A8 | 9/2015 |
| AU | 2013364131 A2 | 10/2015 |
| AU | 2014357428 B2 | 5/2019 |
| AU | 2013364131 B2 | 7/2019 |
| AU | 2018258679 A1 | 11/2019 |
| AU | 2018295533 A1 | 1/2020 |
| BR | 112015015024 A2 | 7/2017 |
| CA | 2310667 A1 | 6/1999 |
| CA | 2379697 A1 | 2/2001 |
| CA | 2438457 A1 | 2/2004 |
| CA | 2772539 A1 | 6/2004 |
| CA | 2683367 A1 | 10/2008 |
| CA | 2506292 C | 5/2012 |
| CA | 2839287 A1 | 1/2013 |
| CA | 2840969 A1 | 1/2013 |
| CA | 2840975 A1 | 1/2013 |
| CA | 2840984 A1 | 1/2013 |
| CA | 3016496 A1 | 1/2013 |
| CA | 2310667 C | 7/2013 |
| CA | 2772539 C | 4/2014 |
| CA | 2896086 A1 | 6/2014 |
| CA | 2933599 A1 | 6/2015 |
| CA | 2945137 A1 | 10/2015 |
| CA | 2982855 A1 | 11/2016 |
| CA | 2840979 C | 7/2018 |
| CA | 3050643 A1 | 7/2018 |
| CA | 3059209 A1 | 11/2018 |
| CA | 3069278 A1 | 1/2019 |
| CA | 2933599 C | 12/2019 |
| CA | 3016496 C | 1/2020 |
| CN | 87102164 | 11/1987 |
| CN | 2585215 Y | 11/2003 |
| CN | 1610516 A | 4/2005 |
| CN | 1697681 A | 11/2005 |
| CN | 1697682 A | 11/2005 |
| CN | 1780655 A | 5/2006 |
| CN | 2839861 A | 11/2006 |
| CN | 101506868 A | 8/2009 |
| CN | 101520690 A | 9/2009 |
| CN | 101681455 A | 3/2010 |
| CN | 101687134 A | 3/2010 |
| CN | 101873824 A | 10/2010 |
| CN | 1780655 B | 12/2010 |
| CN | 101520690 B | 7/2011 |
| CN | 101141567 B | 12/2012 |
| CN | 103448727 A | 12/2013 |
| CN | 103534664 A | 1/2014 |
| CN | 101543047 B | 2/2014 |
| CN | 103764021 A | 4/2014 |
| CN | 103781405 A | 5/2014 |
| CN | 103781409 A | 5/2014 |
| CN | 104235038 A | 12/2014 |
| CN | 204226229 U | 3/2015 |
| CN | 104951225 A | 9/2015 |
| CN | 104969227 A | 10/2015 |
| CN | 105269352 A | 1/2016 |
| CN | 205237581 U | 5/2016 |
| CN | 205302544 U | 6/2016 |
| CN | 205344448 U | 6/2016 |
| CN | 205578301 U | 9/2016 |
| CN | 205578306 U | 9/2016 |
| CN | 205644217 U | 10/2016 |
| CN | 106075696 A | 11/2016 |
| CN | 106102571 A | 11/2016 |
| CN | 106455927 A | 2/2017 |
| CN | 103477340 B | 3/2017 |
| CN | 106574784 A | 4/2017 |
| CN | 106793238 A | 5/2017 |
| CN | 106887110 A | 6/2017 |
| CN | 106913326 A | 7/2017 |
| CN | 106931478 A | 7/2017 |
| CN | 206459246 U | 9/2017 |
| CN | 206655848 U | 11/2017 |
| CN | 108348148 A | 7/2018 |
| CN | 105373219 B | 9/2018 |
| CN | 109171755 A | 1/2019 |
| CN | 110292696 A | 10/2019 |
| CN | 110431509 A | 11/2019 |
| CN | 110604580 A | 12/2019 |
| CN | 107430497 B | 3/2020 |
| CN | 111792030 A | 10/2020 |
| DE | 573822 C | 4/1933 |
| DE | 3723019 A1 | 1/1989 |
| DE | 29605889 U1 | 6/1996 |
| DE | 19936893 A1 | 2/2001 |
| DE | 10037227 A1 | 2/2002 |
| DE | 19936893 C2 | 8/2002 |
| DE | 102005042268 A1 | 5/2006 |
| DE | 102007021564 A1 | 11/2008 |
| DE | 202006020670 U1 | 7/2009 |
| DE | 102008016768 A1 | 10/2009 |
| DE | 102008030790 A1 | 12/2009 |
| DE | 102014103377 A1 | 9/2014 |
| DE | 102014103397 A1 | 9/2014 |
| DE | 102016116761 A1 | 3/2017 |
| DE | 102017204049 B3 | 5/2018 |
| DE | 102018115858 A1 | 1/2020 |
| EP | 0420620 A2 | 4/1991 |
| EP | 885645 | 12/1998 |
| EP | 0885645 A2 | 12/1998 |
| EP | 1032906 A1 | 9/2000 |
| EP | 1157731 | 11/2001 |
| EP | 1157731 A1 | 11/2001 |
| EP | 0885645 B1 | 1/2005 |
| EP | 1707928 A1 | 10/2006 |
| EP | 1895892 A1 | 3/2008 |
| EP | 1340071 B1 | 3/2009 |
| EP | 2136682 A1 | 12/2009 |
| EP | 2138060 A2 | 12/2009 |
| EP | 2197530 A2 | 6/2010 |
| EP | 2266093 A2 | 12/2010 |
| EP | 2058787 B1 | 12/2013 |
| EP | 2729052 A1 | 5/2014 |
| EP | 2729054 A1 | 5/2014 |
| EP | 2729056 A1 | 5/2014 |
| EP | 2751751 A1 | 7/2014 |
| EP | 2773410 A1 | 9/2014 |
| EP | 2861139 A1 | 4/2015 |
| EP | 2895224 A1 | 7/2015 |
| EP | 0936362 A2 | 10/2015 |
| EP | 1636076 B1 | 12/2015 |
| EP | 2613838 | 3/2016 |
| EP | 2613838 B1 | 3/2016 |
| EP | 1661596 B1 | 5/2016 |
| EP | 2138060 B1 | 6/2016 |
| EP | 3069279 A1 | 9/2016 |
| EP | 3082977 A2 | 10/2016 |
| EP | 3117355 A1 | 1/2017 |
| EP | 3129949 A2 | 2/2017 |
| EP | 2197530 | 4/2017 |
| EP | 1850917 | 6/2017 |
| EP | 1850917 B1 | 6/2017 |
| EP | 3282382 A1 | 2/2018 |
| EP | 3283165 A1 | 2/2018 |

(56) References Cited

FOREIGN PATENT DOCUMENTS

| | | |
|---|---|---|
| EP | 3286910 A1 | 2/2018 |
| EP | 3294120 A1 | 3/2018 |
| EP | 3316769 A1 | 5/2018 |
| EP | 3316770 A1 | 5/2018 |
| EP | 2729051 B1 | 6/2018 |
| EP | 3372910 A1 | 9/2018 |
| EP | 2058162 B1 | 1/2019 |
| EP | 2936362 B1 | 3/2019 |
| EP | 3578220 | 12/2019 |
| EP | 3578220 A1 | 12/2019 |
| EP | 3614946 A1 | 3/2020 |
| EP | 3616040 A1 | 3/2020 |
| EP | 3627261 A1 | 3/2020 |
| EP | 3634538 A1 | 4/2020 |
| EP | 3638557 A1 | 4/2020 |
| FR | 2865655 A1 | 8/2005 |
| FR | 2865655 B1 | 4/2006 |
| GB | 1270296 A | 4/1972 |
| IN | 201202311 P4 | 5/2013 |
| IN | 201504225 P4 | 7/2016 |
| IN | 1201647029095 A | 10/2016 |
| IN | 201721043516 A | 12/2017 |
| IN | 201947043607 A | 11/2019 |
| JP | 63-134026 | 6/1988 |
| JP | 2-58091 A | 2/1990 |
| JP | 6-93850 | 4/1994 |
| JP | 10-66820 | 3/1998 |
| JP | 10104190 A | 4/1998 |
| JP | 2001095920 A | 4/2001 |
| JP | 3348956 B2 | 11/2002 |
| JP | 2003-024269 | 1/2003 |
| JP | 2004258828 A | 9/2004 |
| JP | 2005098571 A | 4/2005 |
| JP | 2005-245735 | 9/2005 |
| JP | 2006153337 A | 6/2006 |
| JP | 2007508572 A | 4/2007 |
| JP | 2007170410 | 7/2007 |
| JP | 2008011933 | 1/2008 |
| JP | 4088313 B2 | 5/2008 |
| JP | 2008113861 A | 5/2008 |
| JP | 2008531218 A | 8/2008 |
| JP | 2008209094 A | 9/2008 |
| JP | 2008-276275 A | 11/2008 |
| JP | 4469972 B2 | 6/2010 |
| JP | 2010119762 A | 6/2010 |
| JP | 2010287576 A | 12/2010 |
| JP | 2011075223 A | 4/2011 |
| JP | 2011106373 A | 6/2011 |
| JP | 2011520170 A | 7/2011 |
| JP | 2012-157812 | 8/2012 |
| JP | 5020358 B2 | 9/2012 |
| JP | 5250037 B2 | 7/2013 |
| JP | 5275955 B2 | 8/2013 |
| JP | 2013218725 A | 10/2013 |
| JP | 2014064771 | 4/2014 |
| JP | 2014523038 A | 9/2014 |
| JP | 2014523039 A | 9/2014 |
| JP | 2014524797 A | 9/2014 |
| JP | 2014225236 A | 12/2014 |
| JP | 2015007083 A | 1/2015 |
| JP | 5711389 B2 | 4/2015 |
| JP | 2015-531310 | 11/2015 |
| JP | 2015-217211 | 12/2015 |
| JP | 2016033154 A | 3/2016 |
| JP | 2016509284 A | 3/2016 |
| JP | 2016197422 A | 11/2016 |
| JP | 2017503571 A | 2/2017 |
| JP | 2017508532 A | 3/2017 |
| JP | 6144238 B2 | 6/2017 |
| JP | 2017105839 A | 6/2017 |
| JP | 2017130833 A | 7/2017 |
| JP | 2017138567 A | 8/2017 |
| JP | 2017143589 A | 8/2017 |
| JP | 2017146065 A | 8/2017 |
| JP | 6203634 B2 | 9/2017 |
| JP | 6252607 B2 | 12/2017 |
| JP | 06299785 B2 | 3/2018 |
| JP | 6307238 | 4/2018 |
| JP | 6310507 B2 | 4/2018 |
| JP | 2018511440 A | 4/2018 |
| JP | 2018122119 A | 8/2018 |
| JP | 2018-531152 | 10/2018 |
| JP | 6465155 B2 | 2/2019 |
| JP | 6483594 B2 | 3/2019 |
| JP | 2019082290 A | 5/2019 |
| JP | 6581667 B2 | 9/2019 |
| JP | 2019207684 A | 12/2019 |
| JP | 2020011074 A | 1/2020 |
| JP | 6709479 | 6/2020 |
| JP | 2002-297807 | 10/2022 |
| KR | 2009069335 A | 6/2009 |
| KR | 2014070553 A | 6/2014 |
| KR | 2014114422 A | 9/2014 |
| KR | 2015117092 A | 10/2015 |
| KR | 20150117092 A | 10/2015 |
| KR | 101816443 B1 | 1/2018 |
| KR | 2018009326 A | 1/2018 |
| KR | 101942785 B1 | 1/2019 |
| KR | 2019019180 A | 2/2019 |
| KR | 2019089405 A | 7/2019 |
| KR | 2019093380 A | 8/2019 |
| KR | 2019112507 A | 10/2019 |
| KR | 102072394 B1 | 2/2020 |
| KR | 2020031433 A | 3/2020 |
| KR | 102103631 B1 | 4/2020 |
| KR | 2020054445 A | 5/2020 |
| MX | 2010005090 A | 5/2010 |
| MX | 2014007304 A | 7/2014 |
| MX | 2015004842 A | 7/2015 |
| MX | 355476 B | 4/2018 |
| NO | 178100 | 10/1995 |
| RU | 2015143725 A | 4/2017 |
| WO | 1997007439 A1 | 2/1997 |
| WO | 1998007930 A1 | 2/1998 |
| WO | 1998056488 A1 | 12/1998 |
| WO | 1998057165 A1 | 12/1998 |
| WO | 1999027483 A1 | 6/1999 |
| WO | 2001008752 A1 | 2/2001 |
| WO | 2004009161 A1 | 1/2004 |
| WO | 2005029452 A2 | 3/2005 |
| WO | 2005071372 A1 | 8/2005 |
| WO | 2006086415 | 8/2006 |
| WO | 2006086415 A2 | 8/2006 |
| WO | 2006086472 | 8/2006 |
| WO | 2006086472 A2 | 8/2006 |
| WO | 2006086522 | 8/2006 |
| WO | 2006086522 A2 | 8/2006 |
| WO | 2006092635 A1 | 9/2006 |
| WO | 2006118654 A1 | 11/2006 |
| WO | 2007072385 A2 | 6/2007 |
| WO | 2007095266 A2 | 8/2007 |
| WO | 2008036159 A1 | 3/2008 |
| WO | 2008128250 A1 | 10/2008 |
| WO | 2008131338 A1 | 10/2008 |
| WO | 2009022320 A2 | 2/2009 |
| WO | 2009032540 | 3/2009 |
| WO | 2009032540 A1 | 3/2009 |
| WO | 2009052704 A1 | 4/2009 |
| WO | 2009/105541 A1 | 8/2009 |
| WO | 2009114249 A2 | 9/2009 |
| WO | 2009148646 A2 | 12/2009 |
| WO | 2010082322 A1 | 7/2010 |
| WO | 2011088539 A1 | 7/2011 |
| WO | 2011017778 A9 | 11/2012 |
| WO | 2012174420 A2 | 12/2012 |
| WO | 2013006615 A1 | 1/2013 |
| WO | 2013006627 A1 | 1/2013 |
| WO | 2013006632 A1 | 1/2013 |
| WO | 2013067223 A1 | 5/2013 |
| WO | 2013134645 A1 | 9/2013 |
| WO | 2013188013 A1 | 12/2013 |
| WO | 2014005106 A1 | 1/2014 |
| WO | 2014041104 A1 | 3/2014 |
| WO | 2014060726 A1 | 4/2014 |

(56) References Cited

FOREIGN PATENT DOCUMENTS

| | | |
|---|---|---|
| WO | 2014071145 A1 | 5/2014 |
| WO | 2014100687 A2 | 6/2014 |
| WO | 2014101824 A1 | 7/2014 |
| WO | 2015073459 A1 | 5/2015 |
| WO | 2015095532 A2 | 6/2015 |
| WO | 2015136502 A1 | 9/2015 |
| WO | 2015157575 A2 | 10/2015 |
| WO | 2016105552 A1 | 6/2016 |
| WO | 2016168119 A1 | 10/2016 |
| WO | 2016172469 A1 | 10/2016 |
| WO | 2016182853 A1 | 11/2016 |
| WO | 2017106636 | 12/2016 |
| WO | 2017004068 A1 | 1/2017 |
| WO | 2017004069 A1 | 1/2017 |
| WO | 2017029396 A1 | 2/2017 |
| WO | 2017101747 A1 | 6/2017 |
| WO | 2017106636 A1 | 6/2017 |
| WO | 2017106644 | 6/2017 |
| WO | 2017106644 A1 | 6/2017 |
| WO | 2017126392 A1 | 7/2017 |
| WO | 2017141774 A1 | 8/2017 |
| WO | 2017218295 A1 | 12/2017 |
| WO | 2018016852 A1 | 1/2018 |
| WO | 2018044959 A1 | 3/2018 |
| WO | 2018200865 A1 | 11/2018 |
| WO | 2018201067 A1 | 11/2018 |
| WO | 2018209112 A1 | 11/2018 |
| WO | 2019008529 A1 | 1/2019 |
| WO | 2019202390 | 10/2019 |
| WO | 2019202390 A1 | 10/2019 |
| WO | 2019236759 A1 | 12/2019 |
| WO | 2020023186 A1 | 1/2020 |
| WO | 2020037375 | 2/2020 |
| WO | 2020037375 A1 | 2/2020 |
| WO | 2020041785 A1 | 2/2020 |
| WO | 2020042639 A1 | 3/2020 |
| WO | 2020086528 A1 | 4/2020 |

OTHER PUBLICATIONS

International Search Report and Written Opinion from PCT/US21/41718 dated Nov. 4, 2021.
Invacare XPO2 Portable TM Portable Oxygen Concentrator Brochure, 2010, 4 pages.
Invacare Platinum Mobile POC1-100B, POC1-100C en Oxygen Concentrator User Manual, 2018, 160 pages.
Invacare SOLO2 TM Transportable Oxygen Concentrator User Manual, 2010, 52 pages.
Invacare Perfecto2 TM V Oxygen Concentrator Brochure, 2009, 2 pages.
Invacare Platinum ™10L Oxygen ConcentratorIRC10LXO2 en HomeFill® System Compatible User Manual, 2016, 36 pages.
Invacare Platinum 10 Oxygen Concentrator Brochure, 2019, 2 pages.
International Search Report and Written Opinion from PCT/US21/41714 dated Nov. 15, 2021 (13 pages).
International Search Report and Written Opinion from PCT/US21/41710 dated Nov. 15, 2021 (16 pages).
International Search Report and Written Opinion from PCT/US21/41711 dated Oct. 21, 2021 (13 pages).
Chinh et al. "Simulation and Experimental Study of a Single Fixed-Bed Model of Nitrogen Gas Generator Working by Pressure Swing Adsorption", MDPI, Processes 2019, retrieved on Sep. 22, 2021, retrieved from <URL: https://www.mdpi.com/2227-9717/7/10/654/.
"RIDL, ""Audible Alerts and Visible Signals for the Inogen One GS"", Inogen One GS blog, Oct. 30, 2019. (12 pages)".
International Search Report and Written Opinion from PCT/US21/41717 dated Oct. 21, 2021.
International Search Report and Written Opinion from PCT/US2021/041718 dated Nov. 4, 2021.
International Search Report and Written Opinion from PCT/US2021/041719 dated Oct. 27, 2021.
International Search Report and Written Opinion from PCT/US2021/041712 dated Dec. 16, 2021.
Invitation to Pay Additional Fees from PCT/US21/41712 dated Oct. 6, 2021 (2 pages).
Office Action for Japanese Patent Application No. 2023-502667 mailed Aug. 28, 2023, with English translation attached.
Office Action from U.S. Appl. No. 17/376,202 dated Jun. 7, 2023.
Office Action from U.S. Appl. No. 17/376,278 dated Aug. 23, 2023.
Notice of Allowance from U.S. Appl. No. 17/376,278 dated Oct. 23, 2023.
Office Action from U.S. Appl. No. 17/376,241 dated Dec. 8, 2023.
Notice of Allowance from U.S. Appl. No. 17/376,253 dated Nov. 24, 2023.
Office Action from U.S. Appl. No. 17/376,202 dated Jan. 3, 2024.
Office action from U.S. Appl. No. 17/376,197 dated May 8, 2024.
Allowance from U.S. Appl. No. 17/736,202 dated Apr. 24, 2024.
Office action from U.S. Appl. No. 17/376,241 dated Jun. 7, 2024.
Office action from Canadian Application No. 3,189,534 dated May 24, 2024.
Office action from Candian Application No. 3189568 dated Jun. 4, 2024.
Search Report from European Application No. 21842676.5 dated Jul. 8, 2024.
Search Report from European Application No. 21843492.6, Jul. 10, 2024.
Office action from Japanese Application No. 2023-502665 dated Mar. 11, 2024.
Office action from Japanese Application No. 2023-502670 dated Mar. 29, 2024.
Office action from Japanese Application No. 2023-502666 dated May 23, 2024.
Office action from Japanese Application No. 2023-502671 dated Mar. 13, 2024.
Britannica, The Editors of Encyclopaedia, "Newton's laws of motion", Encyclopedia Britannica, Mar. 28, 2024, 2 pgs., https://www.britannica.com/science/Newtons-laws-of-motion (Year 2024).
Canadian Office action from 3, 189,535 dated Apr. 29, 2024.
Canadian Office action from 3,189,573 dated May 24, 2024.
Canadian Office action from 3, 189,540 dated Apr. 30, 2024.
Office action from Japanese Application No. 2023-502670 dated Aug. 7, 2024.
Office action from Canadian Application No. 3189542 dated Aug. 2, 2024.
Search Report from European Application No. 21843561.8 dated Jun. 27, 2024.
Office action from U.S. Appl. No. 17/376,205 dated Aug. 9, 2024.
Office action from Japanese Application No. 2023-502671 dated Jul. 31, 2024.

\* cited by examiner

SYSTEM AND METHOD FOR CONCENTRATING GAS

CROSS-REFERENCES TO RELATED APPLICATIONS

This application claims priority to U.S. Prov. Pat. App. Ser. No. 63/052,700 titled "System and Method for Concentrating Gas", filed Jul. 16, 2020.

This application incorporates by reference the following patent applications: U.S. Prov. Pat. App. Ser. No. 63/052,694 titled "System and Method for Concentrating Gas"; U.S. Prov. Pat. App. Ser. No. 63/052,700 titled "System and Method for Concentrating Gas"; U.S. Prov. Pat. App. Ser. No. 63/052,869 titled "System and Method for Concentrating Gas"; U.S. Prov. Pat. App. Ser. No. 63/052,533 titled "System and Method for Concentrating Gas"; and U.S. Prov. Pat. App. Ser. No. 63/052,647 titled "System and Method for Managing Medical Devices", all filed on Jul. 16, 2020.

BACKGROUND

Various applications exist for the separation of gaseous mixtures. For example, the separation of nitrogen from atmospheric air can provide a highly concentrated source of oxygen. These various applications include the provision of elevated concentrations of oxygen for medical patients and flight personnel. Hence, it is desirable to provide systems that separate gaseous mixtures to provide a concentrated product gas, such as a breathing gas with a concentration of oxygen.

Several existing product gas or oxygen concentrating systems and methods, for example, are disclosed in U.S. Pat. Nos. 4,449,990, 5,906,672, 5,917,135, 5,988,165, 7,294,170, 7,455,717, 7,722,700, 7,875,105, 8,062,003, 8,070,853, 8,668,767, 9,132,377, 9,266,053, and 10,010,696 which are commonly assigned to Invacare Corporation of Elyria, Ohio and fully incorporated herein by reference.

Such systems are known to be either stationary, transportable, or portable. Stationary systems are intended to remain in one location such as, for example, a user's bedroom or living room. Transportable systems are intended to be moved from location to location and often include wheels or other mechanisms to facilitate movement. Portable systems are intended to be carried with the user such as, for example, via a shoulder strap or similar accessory.

Typically, such systems include various components such as compressors, pumps, valves, sieve beds, and storage tanks. The operation of these components in the gas separation process to produce, for example, medical grade oxygen, generates noise and heat that can adversely impact component life. Also, assembly of such oxygen concentrating systems into a working unit requires additional components whose only function is to provide structural or mounting support, which adds weight, cost and complexity to the oxygen concentrating system. What is desired is an oxygen concentrating system that addresses these and other aspects of the system.

SUMMARY

Gas concentrating systems and methods are provided. In one embodiment, a gas concentrating system is provided that includes component heat management. The heat management system can include, for example, one or more air cooling paths. The air cooling paths direct cooling air into and out of component spaces having heat-generating mechanisms. In other embodiments, the heat management system can also include component spaces that are insulated against the heat of heat-generating components. By cooling heat-generating components and insulating other components from heat, reduced wear and extended component life can be achieved. This reduces component failure and costly service to repair or replace failed or worn components.

In another embodiment, a gas concentrating system and method is provided that includes a mounting body. The mounting body can be unitary or composed of multiple portions. In one embodiment, the mounting body has recesses or spaces formed to accept and retain system components without the use of fasteners. The recesses or spaces can include both recesses and spaces that are formed to tightly hold components in place and those that allow for some movement of the components. In yet other embodiments, the spaces can be air passageways for introducing and exiting cooling air to and from heat generating component spaces. In yet still other embodiments, the recesses or spaces can be insulated spaces for insulating components from the heat generated by heat-generating components. In further embodiments, separate cooling air streams or directed flows can isolate sub-components of an assembly or device from heat. For example, one or more cooling air flows can be directed to individual components of a compressor such as the sleeves and motor to isolate each component from the other. In this manner, even within a common recess or space, heat generated from one area does not transfer directly to another area or component within the space. Other embodiments are further disclosed.

It is an object to provide systems and methods for heat management.

It is another object to provide systems and methods for providing one or more cooling air flow paths.

It is another object to provide systems and methods for providing the exit of one or more cooling air flow paths.

It is another object to provide systems and methods for isolating heat-generating components.

It is another object to provide systems and methods for retaining components without the use of fasteners.

It is another object to provide systems and methods having a mounting body with cooling air flow passageways.

It is another object to provide systems and methods have reduced vibration, noise and/or acoustic levels during operation.

These and other objects, features and advantages will become evident after a review of the following descriptions, drawings, and

BRIEF DESCRIPTION OF THE DRAWINGS

In the accompanying drawings which are incorporated in and constitute a part of the specification, embodiments of the inventions are illustrated, which, together with a general description of the inventions given above, and the detailed description given below, serve to example the principles of the inventions.

DESCRIPTION

As described herein, when one or more components are described or shown as being connected, joined, affixed, coupled, attached, or otherwise interconnected, such interconnection may be direct as between the components or may be indirect such as through the use of one or more intermediary components. Also, as described herein, reference to a member, component, or portion shall not be limited to a single structural member, component, element, or portion but can include an assembly of components, members, elements, or portions.

Embodiments of the present inventions provide, for example, the ability to manage heat generated by the gas concentrating system components. This includes providing one or more air cooling paths. The air cooling paths direct cooling air to component spaces having heat-generating mechanisms. Cooling fans or other mechanisms may be provided to direct cooling air into and out of component spaces where it is required. In other embodiments, the ability to insulate component spaces from the heat of heat-generating components is provided. By cooling heat-generating components and insulating other components from heat, component life can be extended because heat can components to deteriorate or wear quicker than otherwise expected. Premature component wear or failure is costly in that time and transportation is required to replace failed or worn components, an extra supply of gas concentrating systems may be necessary in order to provide the patient with a substitute system during the time it takes to repair such components, and the number of repair components that must be inventoried may be larger than otherwise required.

Embodiments of the present inventions also provide, for example, a gas concentrating system and method for efficiently mounting components. This includes with or without the use of tools and fasteners. In one embodiment, a mounting body is provided within the system housing. The mounting body can include spaces and/or recesses that are molded to the shape of various components (or portions thereof). In this manner, the mounting body spaces can securely receive and retain system components without having the need for fasteners (e.g., screws, bolts, mounting brackets, and the like). For certain components (e.g., sieve beds and product tanks), the mounting spaces/recesses are formed to tightly hold components in place. For other components, (e.g., compressors and pumps), the mounting spaces/recesses are formed slightly larger than the components to allow for some movement of the components. This prevents and/or reduces any vibrations generated by the components from being transmitted to the mounting body. In yet other embodiments, the mounting body spaces/recesses can be air passageways for allowing cooling air to and from heat-generating component spaces. In yet still other embodiments, the recesses or spaces can be insulated spaces for insulating components from the heat generated by heat-generating components.

Figure 1:
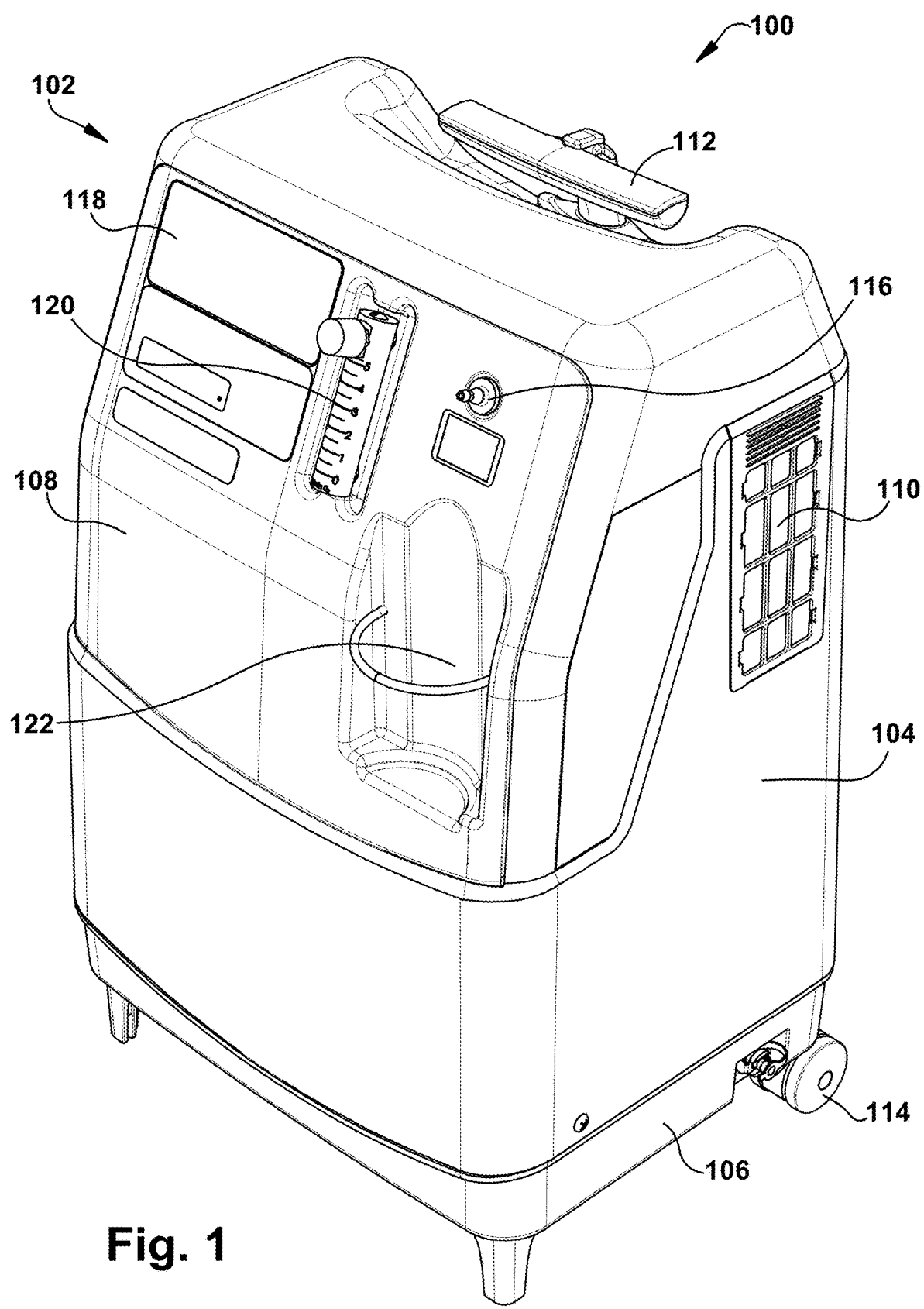
FIG. 1 shows of one embodiment of the gas concentrating system.

Illustrate FIG. 1 is one embodiment of an oxygen system 100. The system may be stationary such as, for example, for use in a hospital or a patient's home. The system can also be ambulatory or mobile such as, for example, for use by a patient when they are away from home. The system can be configured in a manner to allow the patient to carry the system such as, for example, through an over the shoulder strap or through an arrangement whereby the system includes a handle and wheels. Other mobility configurations are also included.

Figure 2A:
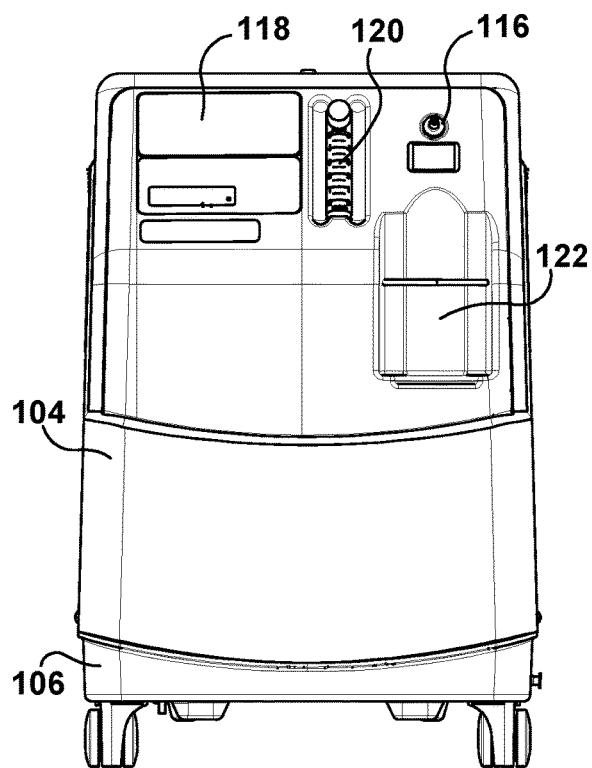
FIGS. 2A-2D show front, back, right, and left side views of the embodiment of FIG. 1.
Figure 2B:
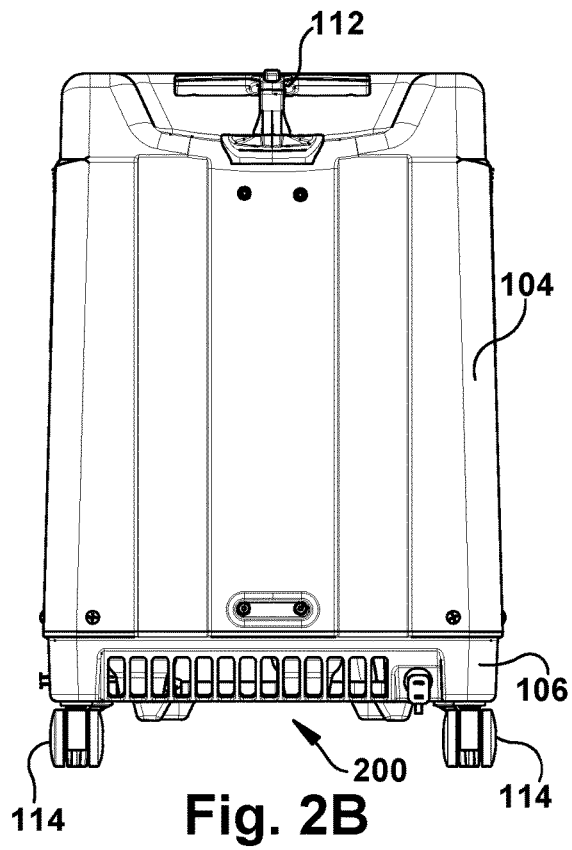
Figure 2C:
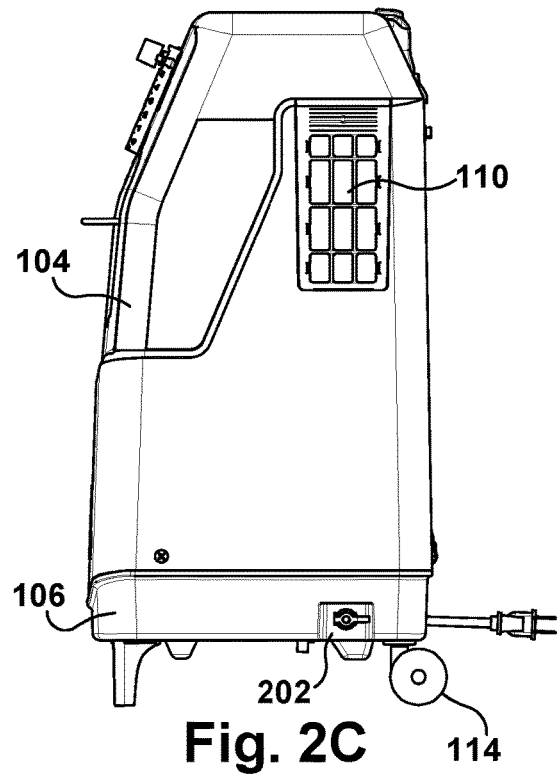
Figure 2D:
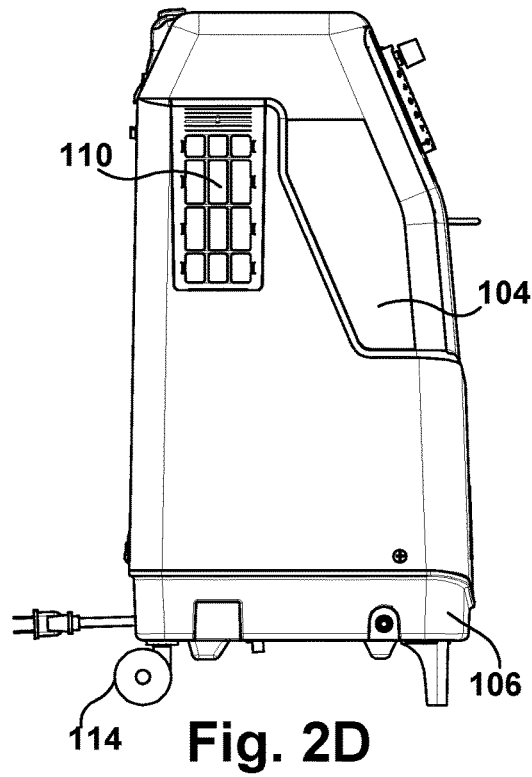

Oxygen system 100 includes a housing 102, which can be in one or more sections. Housing 102 includes a plurality of openings for the intake and discharge of various gases such as, for example, the intake of room air and the discharge of nitrogen and other gases. Oxygen system 100 generally intakes room air from intakes 110, which is mostly comprised of oxygen and nitrogen, and separates the nitrogen from the oxygen by using sieve beds (308 and 310; FIG. 3) The oxygen is stored in one or more internal or external storage or product tanks (302; FIG. 3) and the nitrogen is discharged back into the room air. For example, the oxygen gas may be delivered through port 116 to a patient through tubing and nasal cannula. Alternatively, the oxygen gas may be delivered through a supplemental port (202; FIG. 2C) to an oxygen cylinder filling device, such as HOMEFILL® that is manufactured by Invacare Corp. of Elyria, Ohio, USA and one example thereof being described in U.S. Pat. No. 5,988,165, which is hereby incorporated by reference.

In the embodiment shown, the housing 102 includes several portions 104 and 106. A panel 108 is also provided having a system display 118, adjustable flowmeter 120, and a recess 122 for an optional humidifier bottle. System 100 may also include an extendable handle 112 and wheels 114 for ease of transport and handling. Housing 102 also includes an exhaust vent 200 (FIG. 2) for exhausting cooling air that has been drawn into the system and used to cool internal components thereof.

Figure 3A:
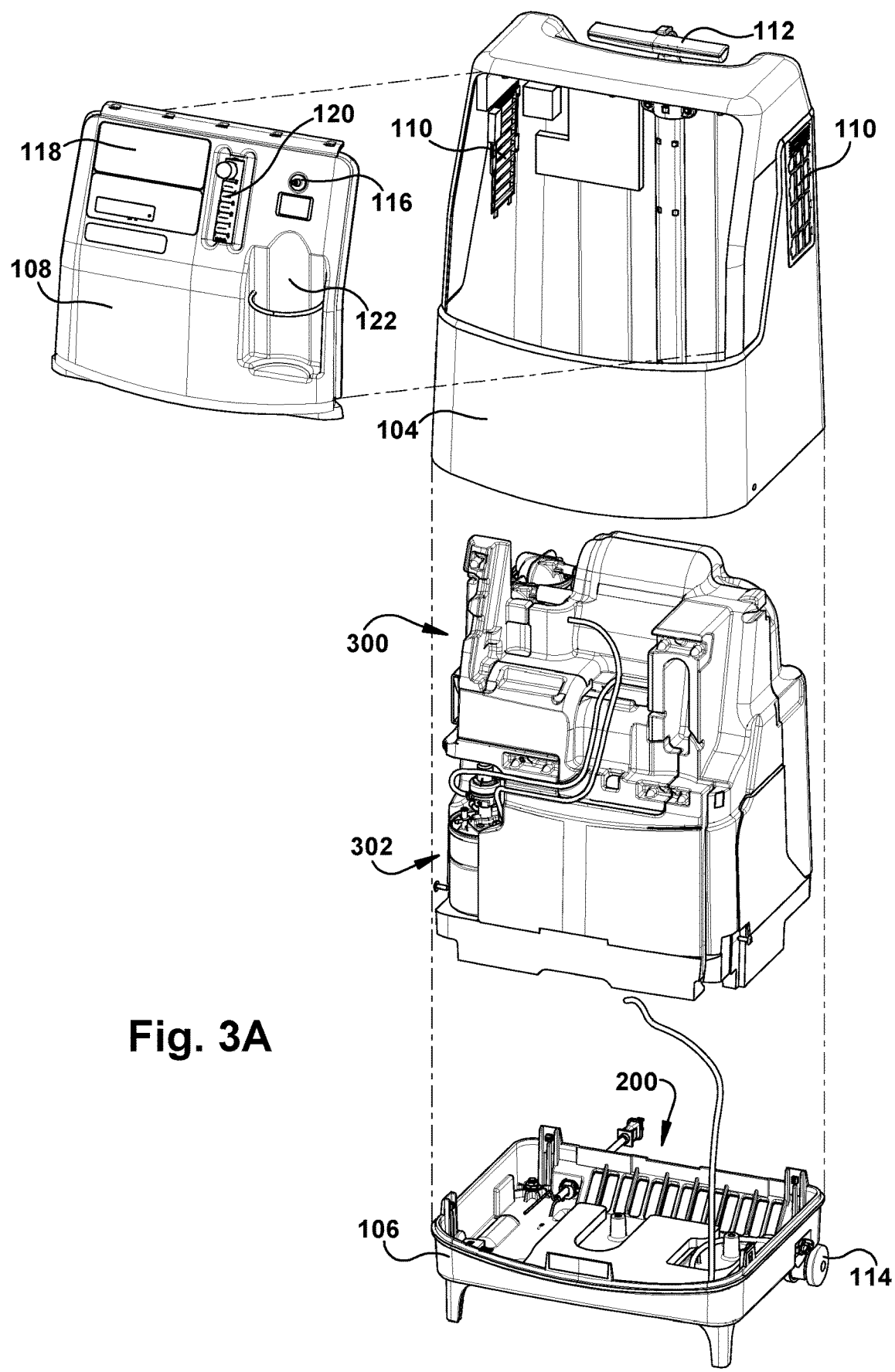
FIGS. 3A-3B are exploded perspective views of the embodiment of FIG. 1.
Figure 3B:
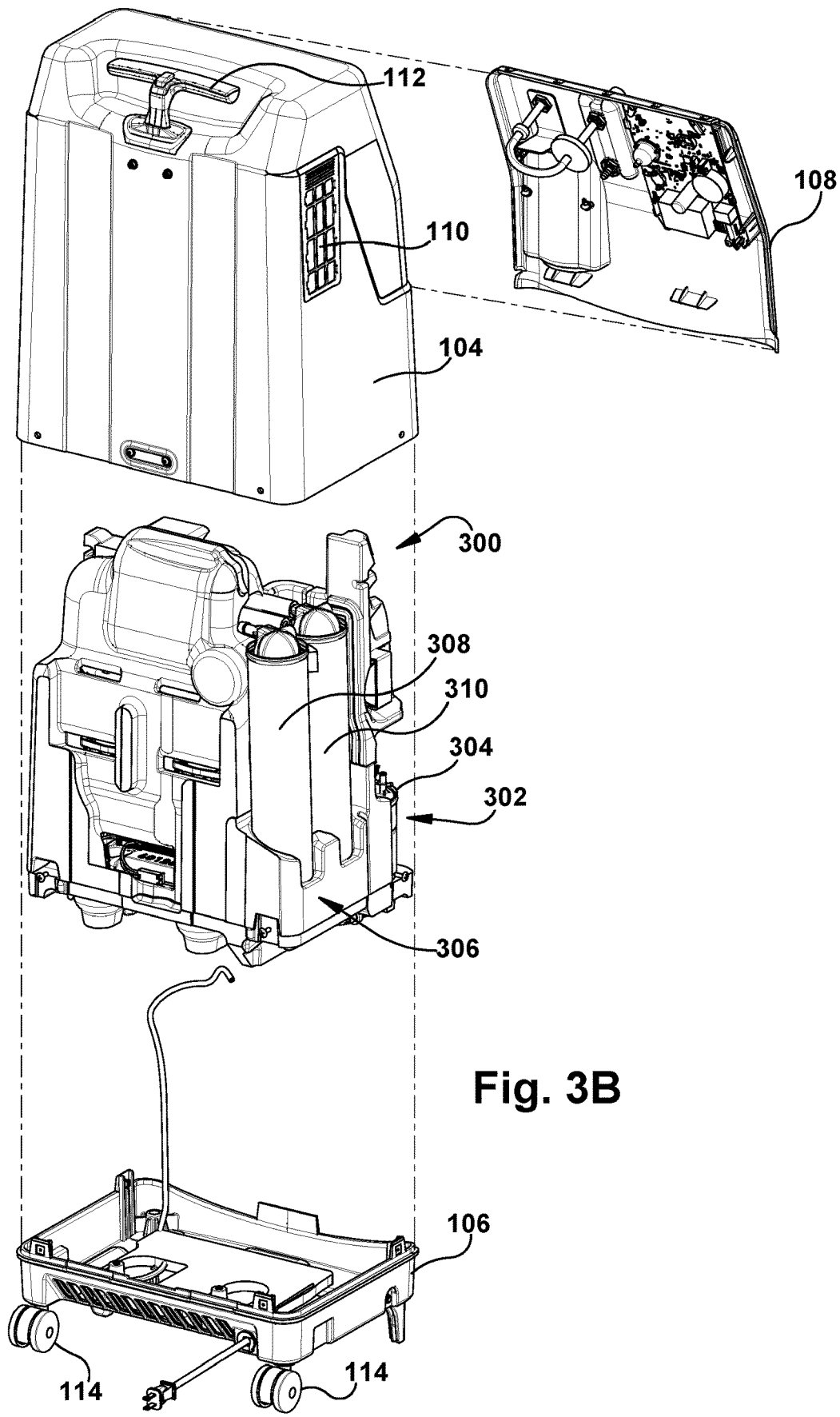
Figure 4A:
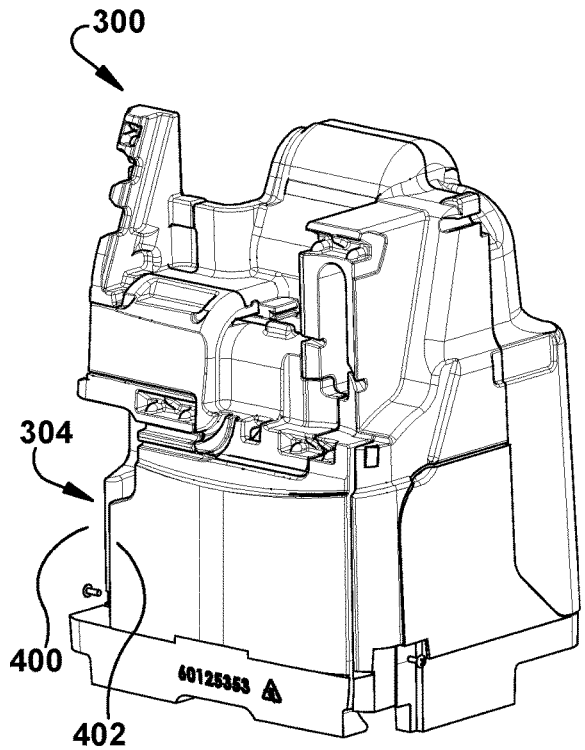
FIGS. 4A-4H are various perspective views of one embodiment of a mounting body.
Figure 4B:
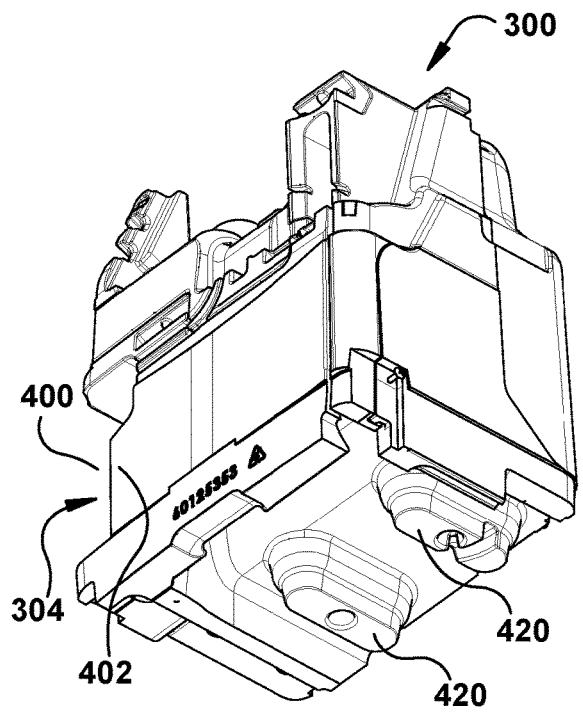
Figure 4C:
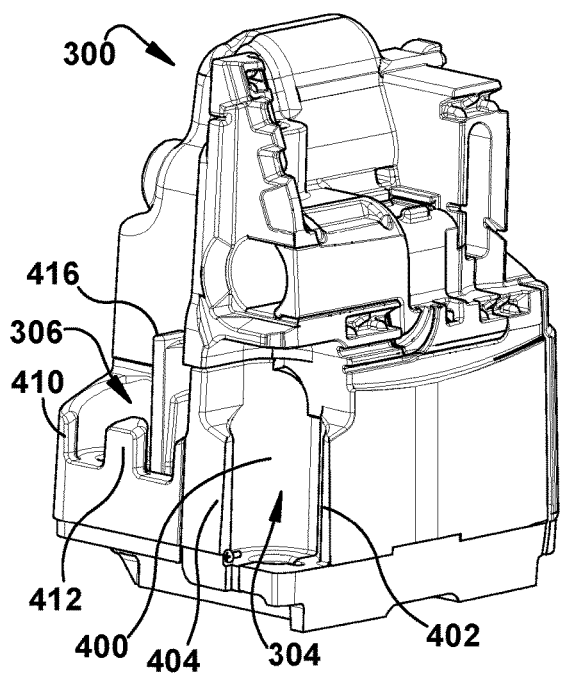
Figure 4D:
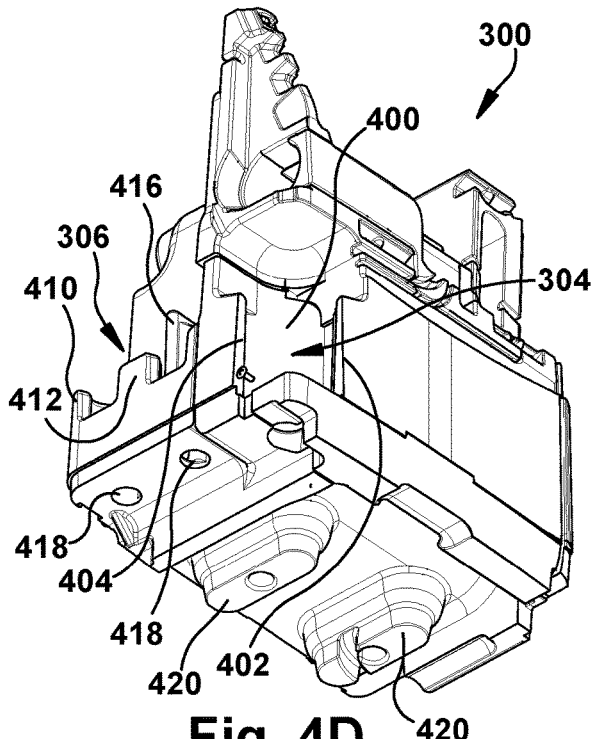
Figure 4E:
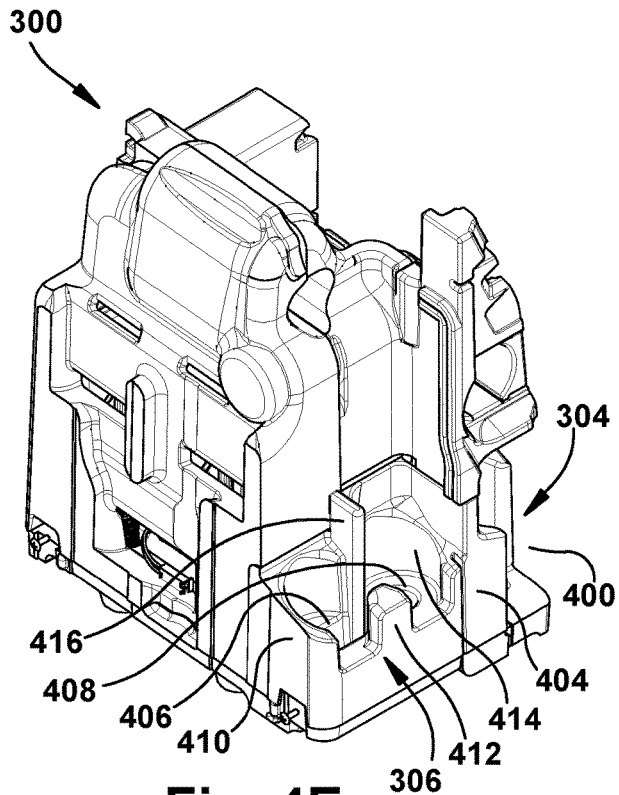
Figure 4F:
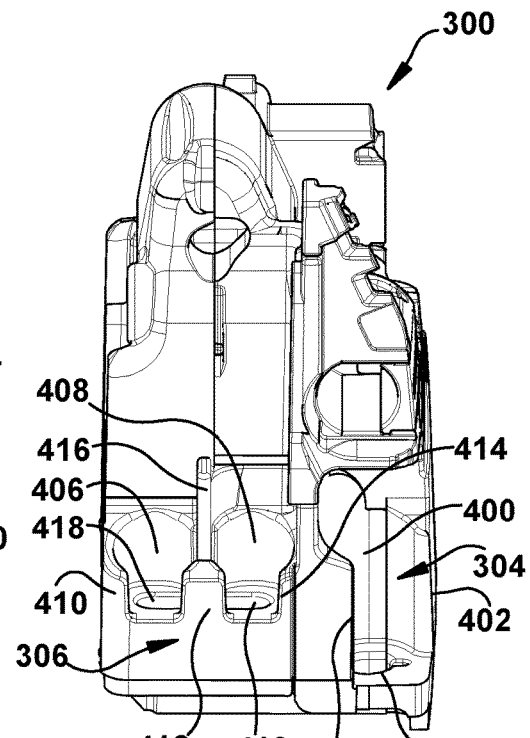
Figure 4G:
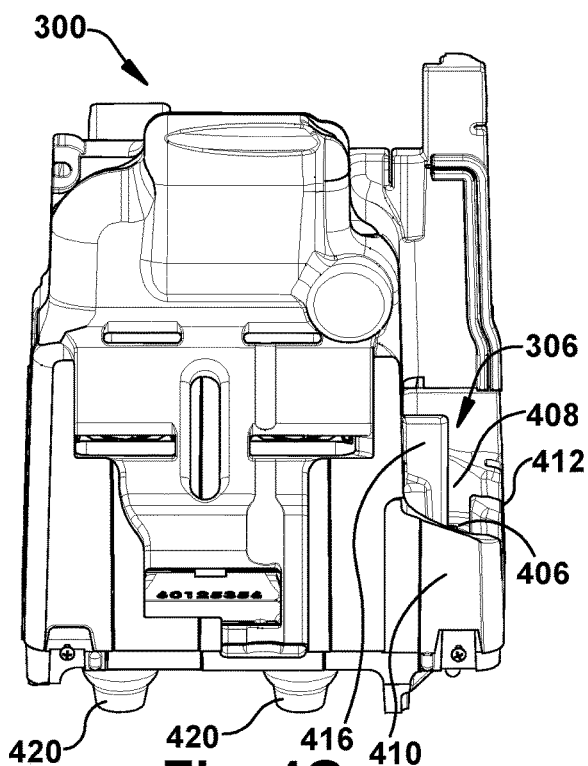
Figure 4H:
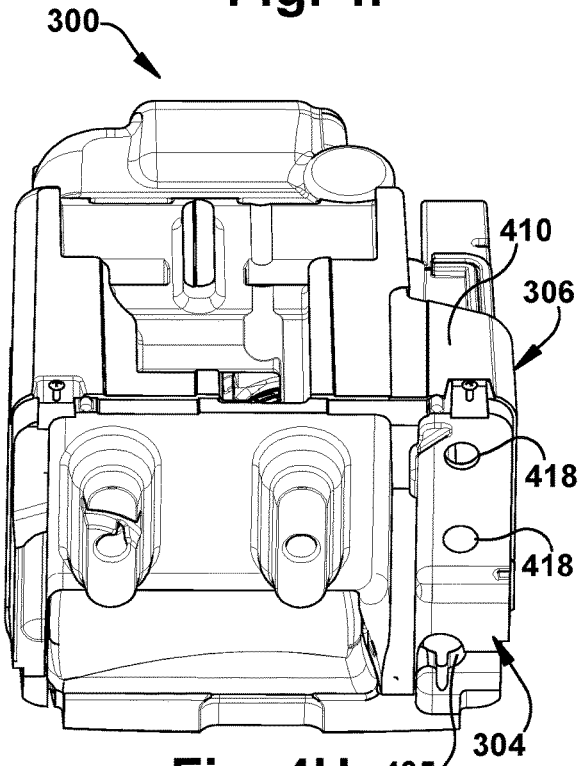

FIGS. 3A and 3B illustrate various exploded perspective views of system 100 and housing 102. As shown in this embodiment, housing portion 104 and housing portion 106 connect together to form an internal space for component mounting body 300. Housing 102 protects various system components that may not be located completely within mounting body 300. This includes, for example, product tank 302 and sieve beds 308 and 310. In the embodiment shown, mounting body 300 includes portion 304 for receiving and securing product tank 302 and portion 306 for receiving and securing sieve beds 308 and 310. In the embodiment shown, mounting body 300 is received and secured to housing portion 106 with or without the use of fasteners.

FIGS. 4A-4H illustrate various perspective views of the external surfaces of mounting body 300 with the gas separation components removed. In this embodiment, the outer or external surfaces of mounting body 300 include spaces/recesses configured to receive and retain components of the gas separation system. For example, a product tank portion 304 for receiving and securing product tank 302 is provided. Portion 304 includes a product tank space 400 for receiving product tank 302. Space 400 includes and is bound by walls 402 and 404, which may be curved to accommodate the shape of the product tank 302 product tank 302 within the space. While walls 402 and 404 are illustrated as only partially extending or encircling the shape of a product tank, in other embodiments walls 402 and 404 can extend or encircle substantially the entire outer shape of a product tank. In this embodiment, product tank space 400 receives and retains product tank 302 without the need for fasteners via a tight or friction fit (or press or interference fit) connection. In other embodiments, fasteners may be used to assist retention of product tank 302. Product tank space 400 further includes an opening 405 for allowing tubing to provide product tank 302 with product gas and/or to allow product gas to exit from product tank 302.

The outer or external surfaces of mounting body 300 can also include a sieve bed mounting space 306. In one embodiment, sieve bed mounting space 306 includes spaces/recesses 406 and 408 for receiving sieve beds 308 and 310. Sieve bed mounting space 306 includes walls 410 and 414 and divider walls 412 and 416. These walls are configured to form spaces/recesses 406 and 408 to at least partially received in retain portions of sieve beds 308 and 310. In one embodiment, these walls are configured to closely mate with the external walls of sieve beds 308 and 310. In the embodiment shown, these walls partially receive the external walls of sieve beds 308 and 310. In other embodiments, these walls can be sized and dimensioned to completely receive sieve beds 308 and 310 such that no portions thereof are exposed. In this embodiment, sieve bed mounting spaces 406 and 408 receive and retain sieve beds 308 and 310 without the need for fasteners and can use a tight or friction fit (or press or interference fit) connection. In other embodiments, fasteners may be used to assist retention of the sieve beds. Sieve bed mounting space 306 also includes one or more openings 418 to allow tubing to carry product gas (such as oxygen) away from the sieve beds and into the product tank 302.

Figure 7:
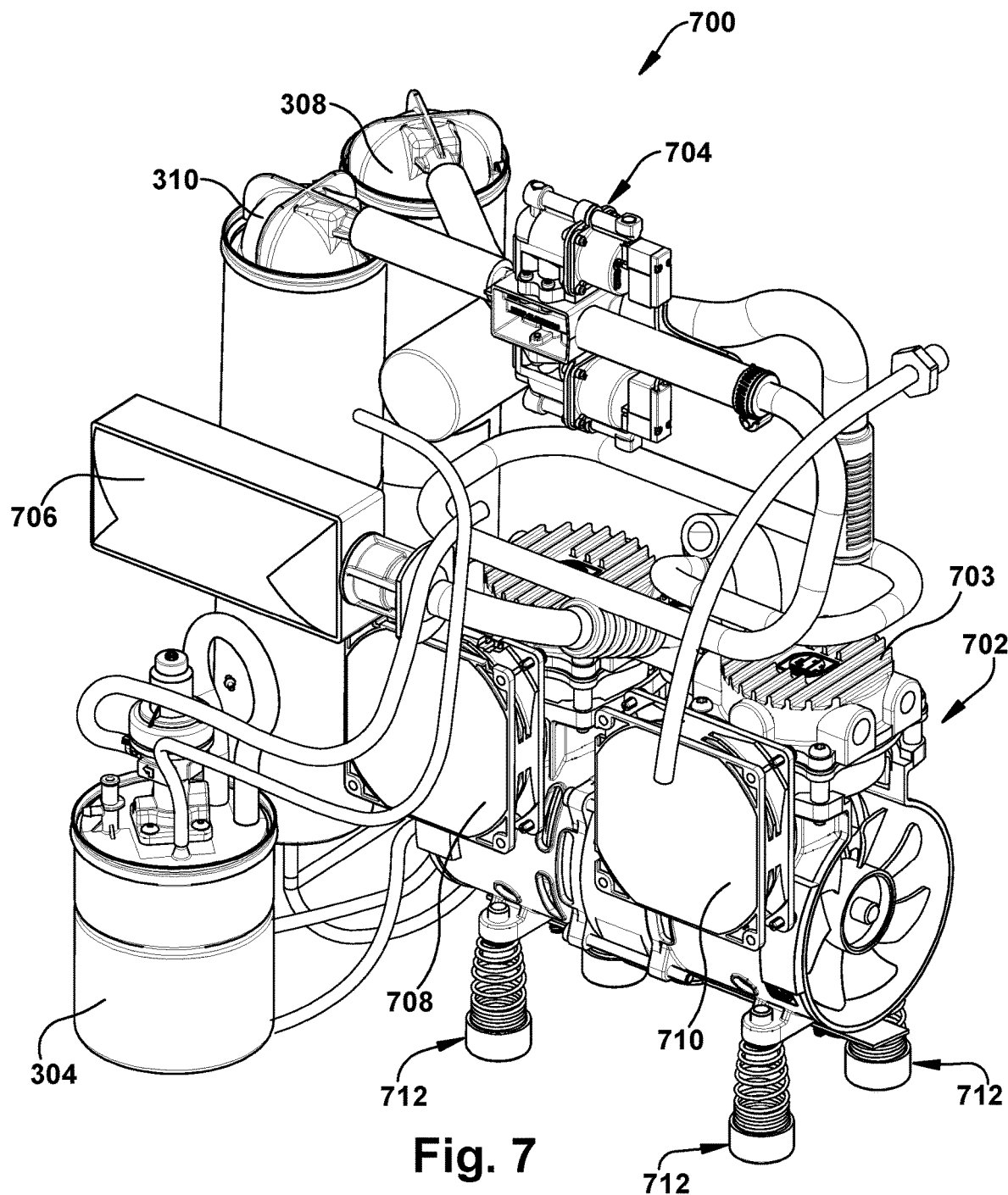
FIG. 7 is a perspective view of the gas concentrating components.

Support stands 420 can also be provided in bottom portion 508 to provide additional structural support to mounting body 300. In one embodiment, Support stands 420 include internal recesses 800 (FIG. 8) for receiving and retaining the compressor systems mounting stands 712 (FIG. 7). Support stands 420 may further include holes (including threaded holes) for affixing bottom portion 508 of mounting body 302 to bottom housing portion 106. In other embodiments, these mounting holes need not be used.

Figure 5A:
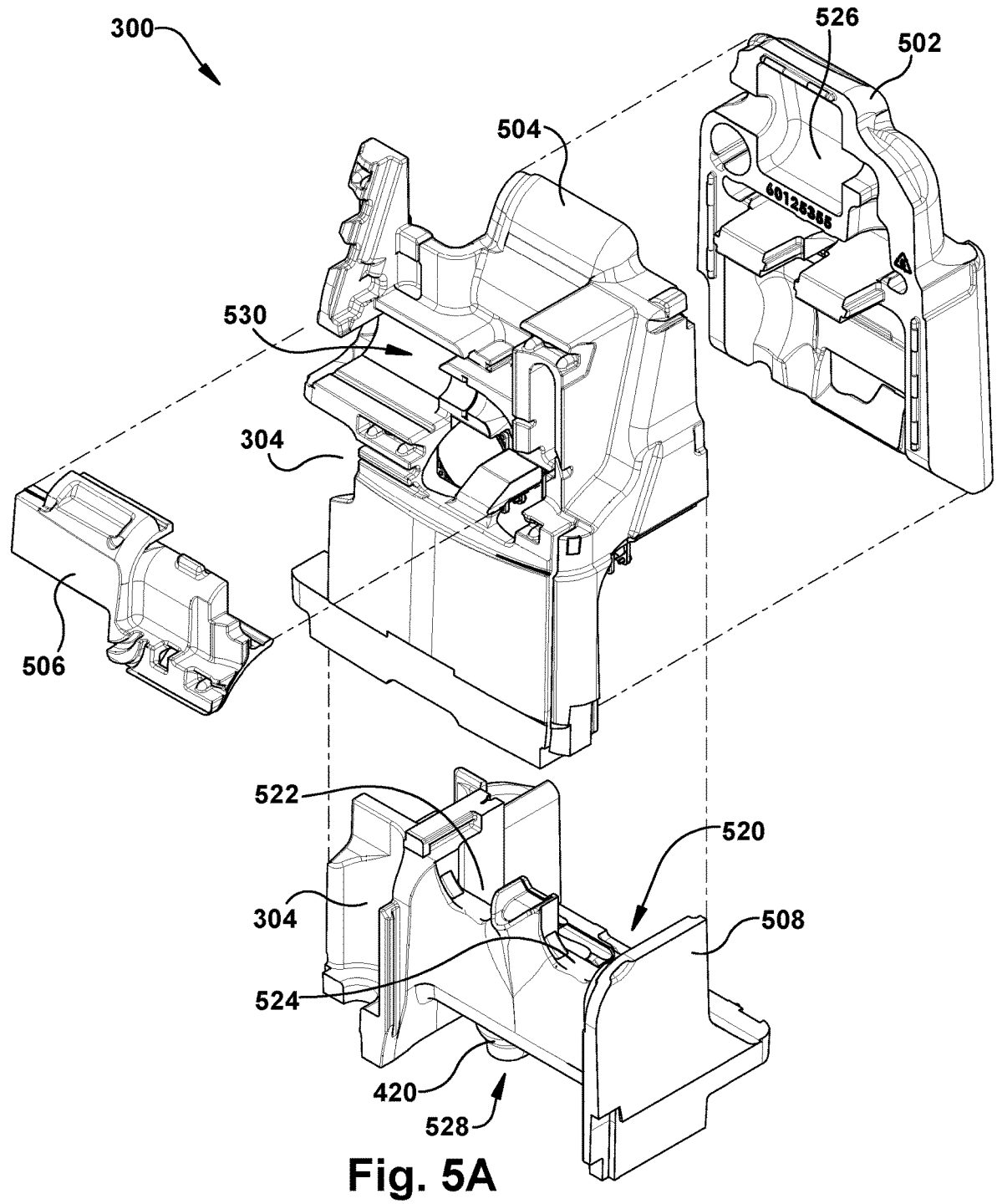
FIGS. 5A-5B are exploded perspective views of the mounting body of FIGS. 4A-4H.
Figure 5B:
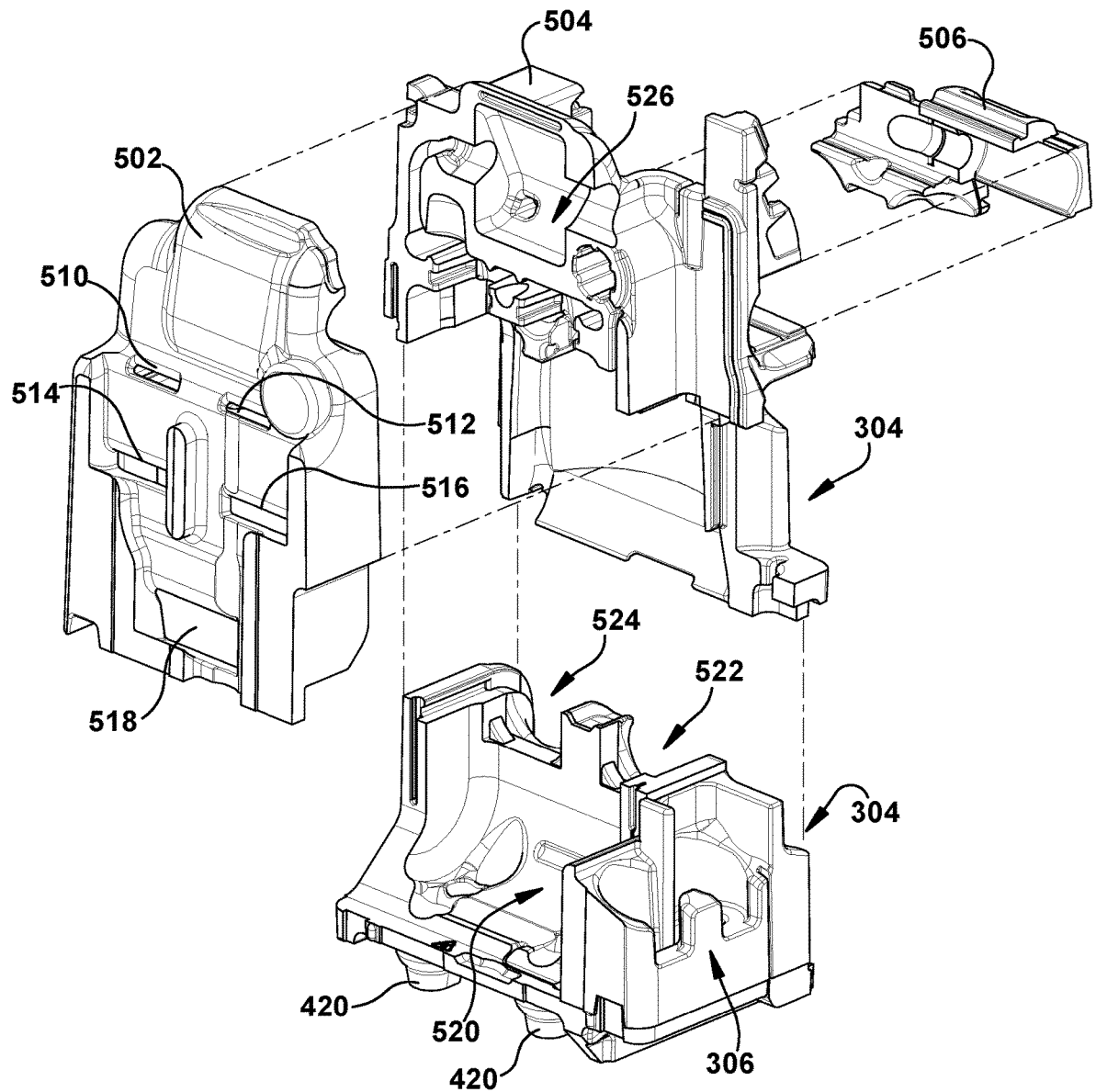

FIGS. 5A and 5B illustrate exploded perspective views of one embodiment of mounting body 300. In this embodiment, mounting body 300 includes multiple portions including back portion 502, front portion 504, filter cover portion 506, and compressor mounting or bottom portion 508. These portions provide mounting body 300 with internal surfaces arranged to provide spaces for receiving and retaining various gas concentrating system components. For example, a compressor space 520 is provided for receiving and retaining a compressor or pump. One or more cooling fan spaces 522 and 524 are also provided for receiving and retaining cooling fans. One or more valves spaces 526 further provided. An exhaust space 528 is also provided for exhausting cooling air after it has passed the heat-generating components. In one embodiment, exhaust space 528 directs air out of the back of the housing 102 and away from the patient or user. A HEPA filter space 530 correspondingly provided for receiving and retaining a HEPA filter for air to be fed into the gas separating system.

Referring to FIG. 5B, body portion 502 includes a plurality of cooling air openings or intakes including upper openings 510 and 512, middle openings 514 and 516, and lower opening by 518. These openings allowed cooling air to be drawn into mounting body 302 cool heat generating components therein. The cooling air is then exhausted out of mounting body 300 through exhaust space 528.

Mounting body portions 502, 504, 506, and 508 are arranged with various projections and recesses along segments of their perimeters. In one embodiment, these projections and recesses (e.g., tongue and groove type arrangements) are configured to provide a friction fit/hold between the mounting body portions to secure and retain them together without the use of fasteners. In other embodiments, fasteners may be used to secure and retain the mounting body portions together.

Figure 6A:
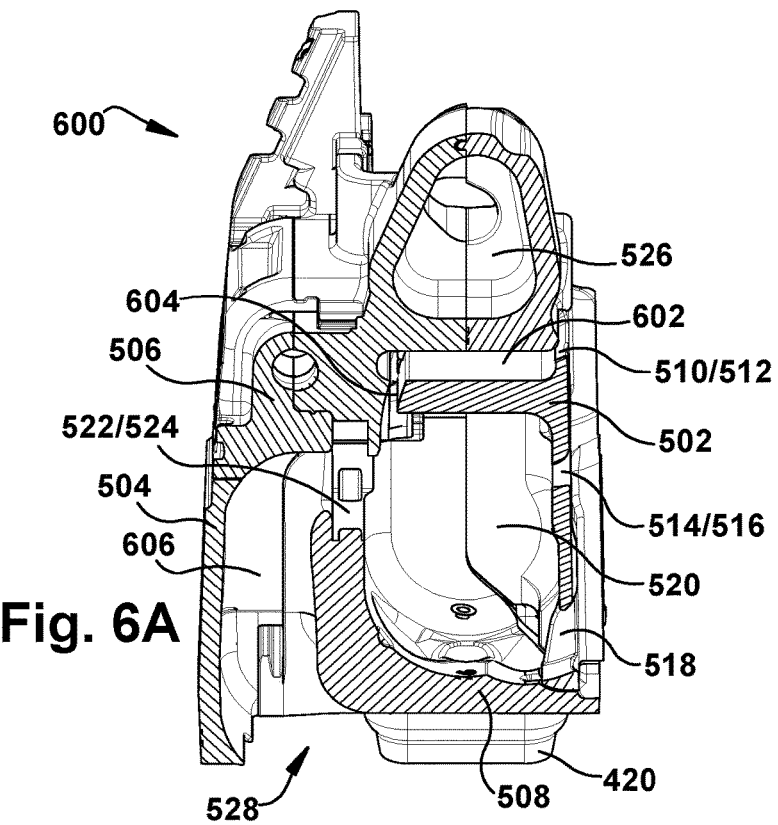
FIGS. 6A-6D are various sectional views of one embodiment of a mounting body having a heat management system.
Figures 6B, 6C:
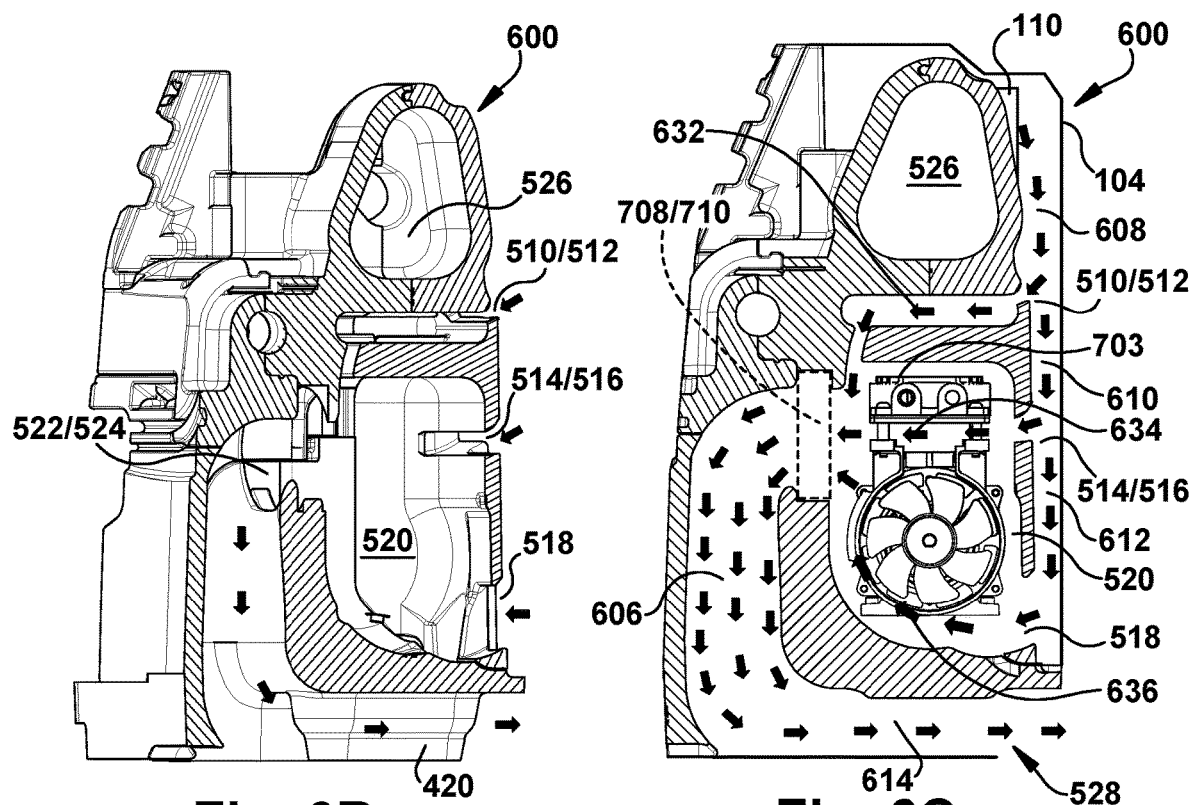

FIG. 6A-6C illustrate one embodiment of a heat management system 600. System 600 includes upper, middle and lower openings 510, 512, 514, 516, and 518. One or more channels or passageways are provided to direct cooling air (represented by arrows in FIGS. 6B and 6C) into and out of the inner space(s) of mounting body 300. This includes channels 602, 604, 608, 610 and 612. One or more cooling fans 708 and 710 draw cooling air in from the exterior of the system via housing air intakes 110. The cooling air flows along passages 608, 610, and 612 and through upper openings 510 and 512, middle openings 514 and 516, and lower opening 518 and into mounting body 300. Passages 608, 610, and 612 are formed by the spaces between the outer surface of mounting body 300 and the inner surface of housing portion 104.

Passages 602 and 604 allow cooling air to flow from upper openings 510 and 512 into compressor space 520. Middle openings 514 and 516 and lower opening 518 allow cooling air to directly enter compressor space 520. In other embodiments, more or less passageways can be provided between the cooling air inlet openings and the space(s) to be cooled. In the embodiment illustrated, compressor space 520 as multiple sources of cooling air (e.g., multiple upper, lower and bottom cooling air intakes). In other embodiments, the number of cooling air sources can be more or less than those shown and can be larger or smaller than those illustrated.

In one embodiment, the mounting body 300 space(s) to be cooled is compressor space 520. Compressor space 520 includes one or more heat generating components such as, for example, a compressor system 702 (FIG. 7). The heat management system 600 is arranged in one embodiment so that cooling air can be drawn by cooling fans 708/710 into compressor space 520 to cool the compressor system 702. Cooling the compressor system reduces wear on the system components (e.g., valves, seals, bearings, electrical insulation, motors, etc.) and prolongs their working life.

As shown in FIG. 6C, one or more directed cooling flow paths or air streams can be generated. This includes streams 632, 634, and 636. One or more streams can be directed to one or more components, subcomponents of an assembly, and/or areas to isolate and manage the heat generated thereby from other components, subcomponents, and/or areas. In one embodiment, airstream 632 is directed to the compressor output tubing or piping to cool the compressed air before it enters the sieve beds. Airstream 636 is directed to the compressor space 520 where the motor component of the compressor resides. In this manner, heat generated by the motor component of the compressor can be isolated and managed within the larger compressor space 520 so that the heat generated thereby is isolated from other compressor components. Similarly, stream 634 is intentionally directed to compressor space 520 where the heat exchanger component (e.g., see also 703 in FIG. 7) of the compressor resides. Stream 634 causes the heat dissipated by heat exchanger 703 to be routed downstream of the compressor to not impact the temperature of the compressor (or its motor and/or piston assembly). In this manner, heat generated by the heat exchanger component 703 of the compressor can be intentionally isolated and managed within the larger compressor space 520 so that heat generated thereby is isolated from other compressor components. Streams 632, 634 and 636 are only one example of providing and using multiple cooling air paths or streams directed to specific areas or components in order to isolate, cool, and manage the heat generated thereby. Additional directed flow paths or air streams can be added. Therefore, one or more directed airflows or cooling air streams can be directed to areas or components within spaces to isolate, cool and manage the heat generated thereby. The heat is dissipated by routing the cooling air streams downstream or away from other components in the system.

Cooling air is exhausted from the inner spaces of mounting body 300 by passages 606 and 614 and out through exhaust space 528. In one embodiment, passage 606 is formed within the inner spaces of mounting body 300 and passage 614 is formed by the space between the outer surfaces of mounting body 300 and the inner surface of housing portion 106. In other embodiments, these passages can be formed completely within mounting body 300 or in combination with the surfaces of mounting body 300 and housing portion 106.

In yet other embodiments, the components residing within the inner spaces of mounting body 300 can include heat conductive surfaces arranged to interact with the directed airflows or cooling air streams. For example, fins or conductive plates can be added to compressor components such as the motor, piston sleeves and heat exchangers. Further yet, the inner spaces of mounting body 300 can include heat conductive wall surfaces or wall coatings forming additional cooling pathways. In one embodiment, the heat conductive wall surfaces or wall coatings work in connection with the cooling air streams to direct heat away from heat generating components. The heat conductive wall surfaces or wall coatings can themselves form a cooling pathway transporting heat from heat generating areas or components to cooler or cooled areas of the device including heat exchangers transferring such heat to the outside of the device.

Figure 6D:
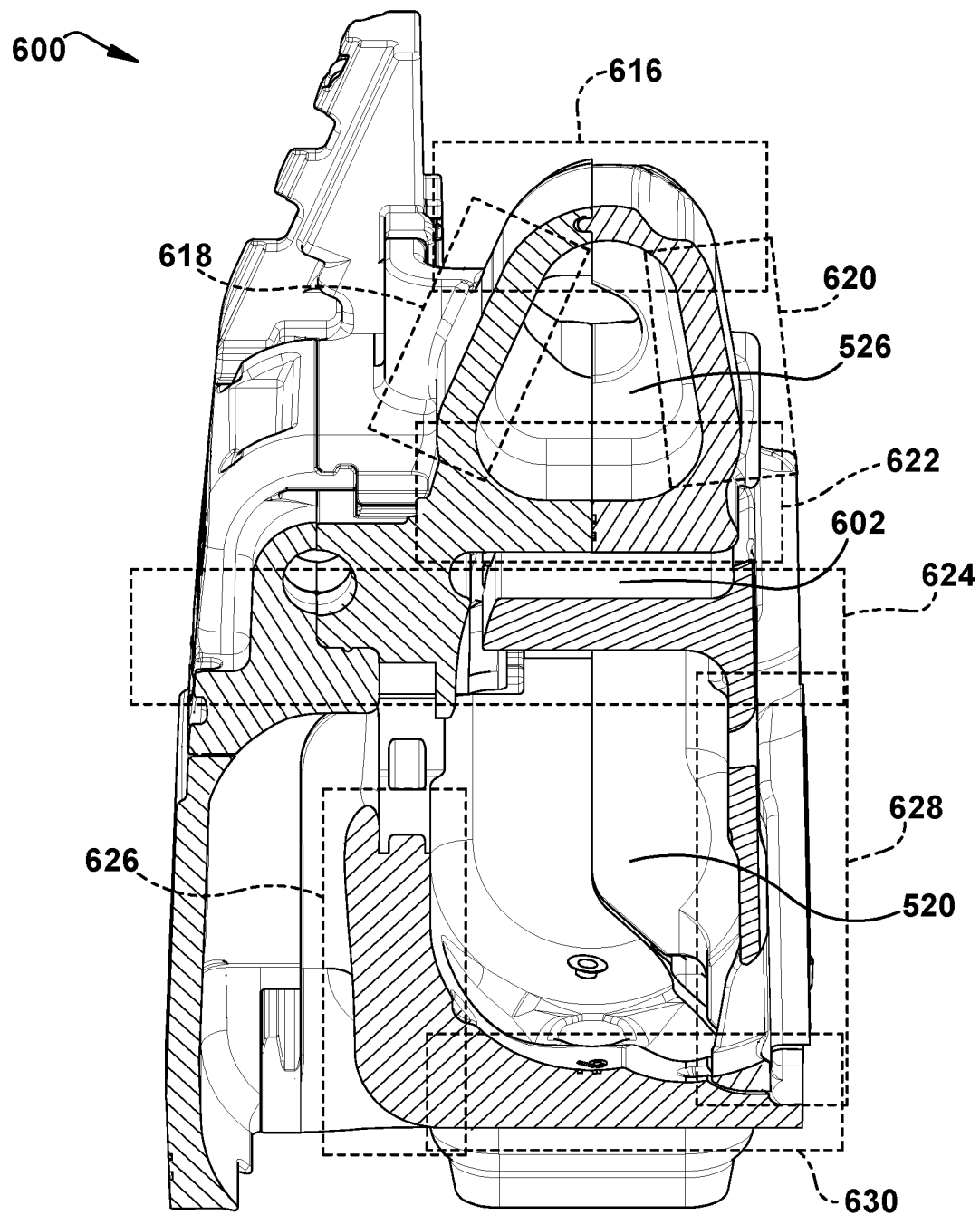

In one embodiment, heat management system 600 includes recesses or spaces that can be insulated spaces for insulating components from the heat generated by heat-generating components. For example, valve space 526 can be thermally insulated from the heat generated within compressor space 520. Also, compressor space 520 can be thermally insulated to contain the heat generated therein. Referring to FIG. 6D, one embodiment of such an arrangement is shown. Valve space 526 can be formed by one or more insulating walls or portions 616, 618, 620, and 622. These walls can be made from any appropriate thermally insulating material and can be dimensioned and sized as appropriately necessary to minimize the transmission of heat into valve space 526.

In the embodiment shown, valve space 526 is thermally insulated from the heat generated by compressor space 520 by wall or portion 622. Valve space 526 is further thermally insulated from the heat generated by compressor space 520 by cooling air passing through passage 602. Passage or space 602 contains the tubing or ducts carrying compressed air from compressor 520 to sieve beds 308 and 310 for the production of oxygen. In other embodiments, valve space 526 may have more or less thermally insulating components (e.g., walls, air cooled passageways, etc.) than those shown. Thermally insulating valve space 526 from heat generating components reduces wear on valve components (e.g., seals, gaskets, stems, etc.) and prolongs their work life.

Compressor space 520 can also be thermally insulated (in addition to air cooled) to minimize the transmission of heat there from to other components. In the embodiment shown, compressor space 520 can be formed by one or more insulating walls or portions 624, 626, 628, and 630. These walls can be made from any appropriate thermally insulating material and can be dimensioned and sized as appropriately necessary to minimize the transmission of heat into valve space 526, product tank holding portion 304, sieve bed holding portion 308, and system electronics associated with panel 108.

In other embodiments, the walls of mounting body 300 discussed herein can also provide acoustic insulation resulting in a quieter gas concentrating system. For example, insulating walls or portions 624, 626, 628, and 630 associated with compressor space 520 may reduce, contain, or absorb vibration and noise generated by the operation of the compressor system. Insulating walls or portions 616, 618, 620, and 622 associated with valve space 526 can also reduce, contain, or absorb vibration and noise generated by the opening and closing action of the valves. The walls of the mounting body 300 may further contain, absorb or reduce the vibration and sound associated with cooling fans 708 and 710 and the movement of cooling air into and out of the system.

Referring now to FIG. 7, various components of an exemplary gas concentrating system 700 is shown. In one embodiment, all these components are mounted to or contained within mounting body 300 without the use of fasteners. In other embodiments, fasteners can be used. The system includes a HEPA filter 706 for filtering air being drawn into compressor system 702. Compressor system 702 feeds compressed air through valve 704 and in an alternating fashion into sieve beds 308 and 310. Sieve beds 308 and 310 separate nitrogen and oxygen from room air and direct the oxygen into product tank 304. Product tank 304 then supplies the oxygen gas to a patient or user. In one embodiment, compressor system 702 includes resilient (e.g., spring based) mounting stands 712 for minimizing vibration caused by operation of the compressor and being transmitted to mounting body 300. The system 700 further includes various tubing for transporting system gases between components and other parts (e.g., silencers/mufflers, filters, etc.) System 700 is operated by processor control system with logic embedded therein and sensors (e.g., pressure, flow, and/or oxygen, etc.) to control the speed of the compressor and timing of the opening and closing of the valves to provide a Pressure Swing Adsorption (or other previously described) gas separation process.

Figure 8A:
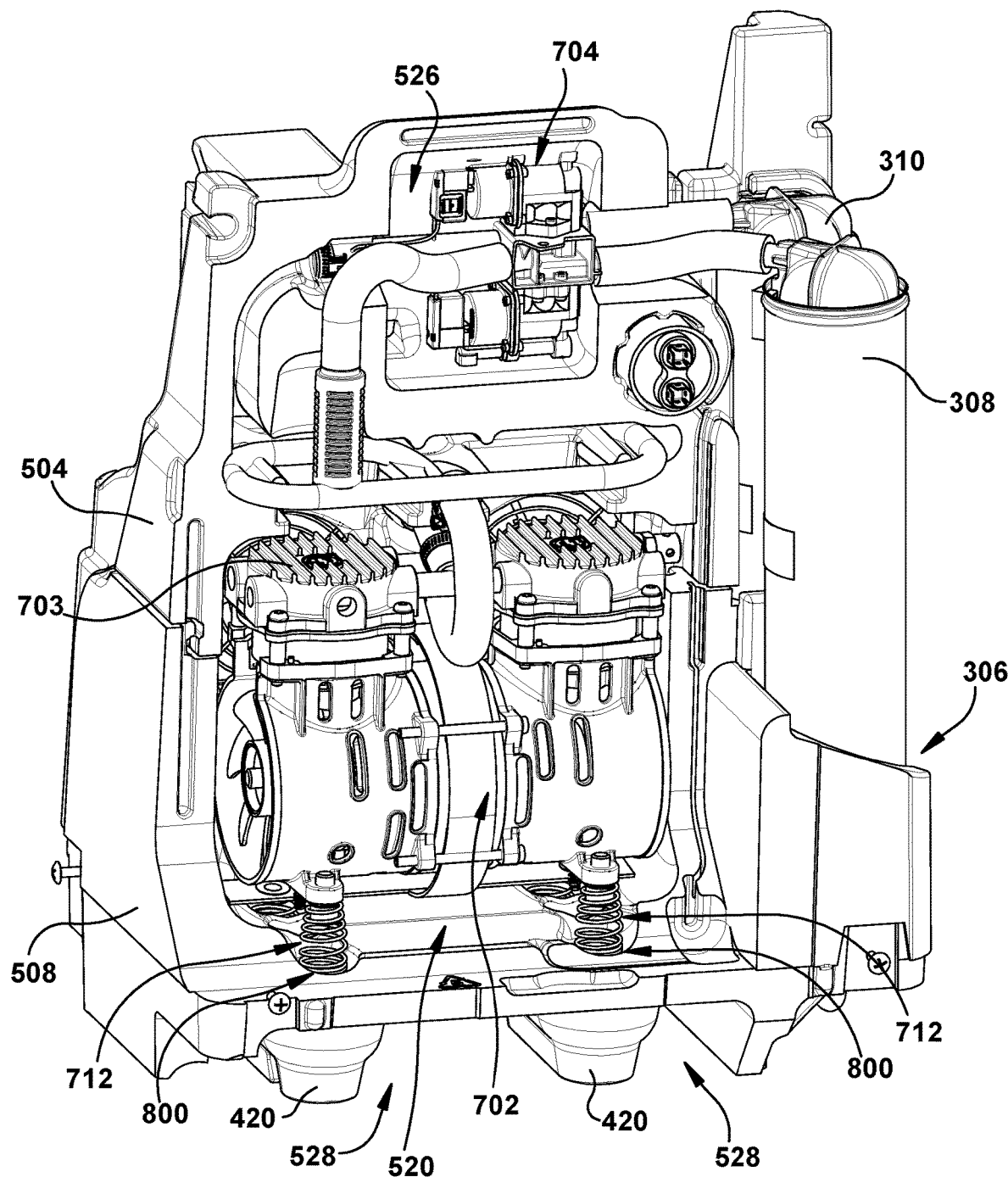
FIGS. 8A-8D are various views of the gas concentrating components arranged within portions of one embodiment of a mounting body.
Figure 8B:
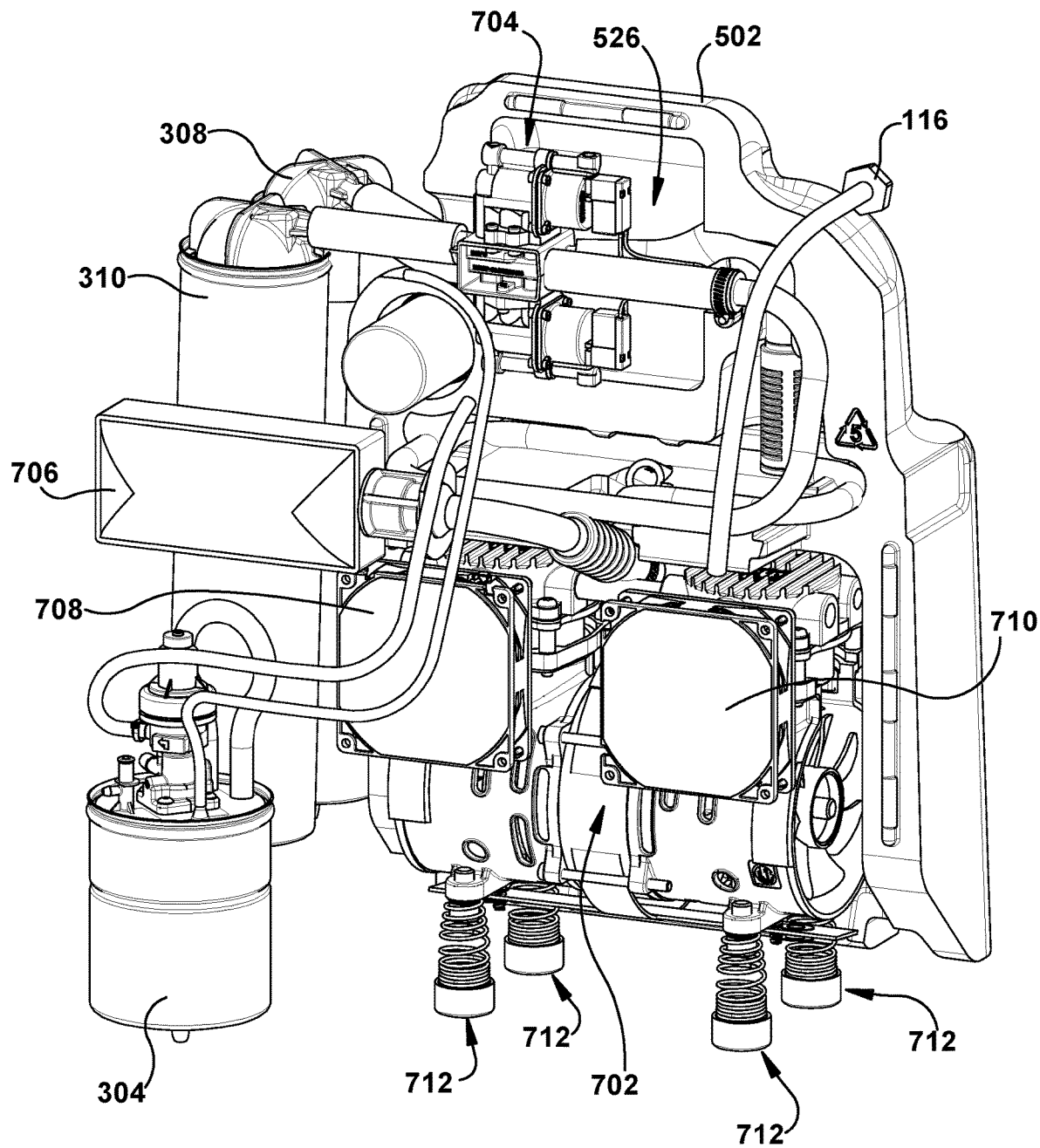

FIGS. 8A and 8B are perspective views of an exemplary gas concentration system mounted to and/or contained within mounting body 300. For example, FIG. 8A shows a perspective view of the gas separation system components in association with back portion 504 and bottom portion 508 of mounting body 300. Compressor system 702 is shown within compressor space 520 and compressor mounting stands 712 shown as being received and retained in recesses 800. Recesses 800 securely receive and retain portions of compressor mounting stands 712 via a tight or friction fit (or press or interference fit) connection in one embodiment.

Valves 704 are shown within valve space 526 formed by back mounting body portion 504. FIG. 8B shows a perspective view of the gas separation system components in association with front mounting body portion 502. As illustrated, valves 704 are shown within the portion of valve space 526 formed by front mounting body portion 502. In other embodiments, valve space 526 need not be can formed by the surface of multiple mounting body portions and can be formed substantially within a single mounting body portion.

Figure 8C:
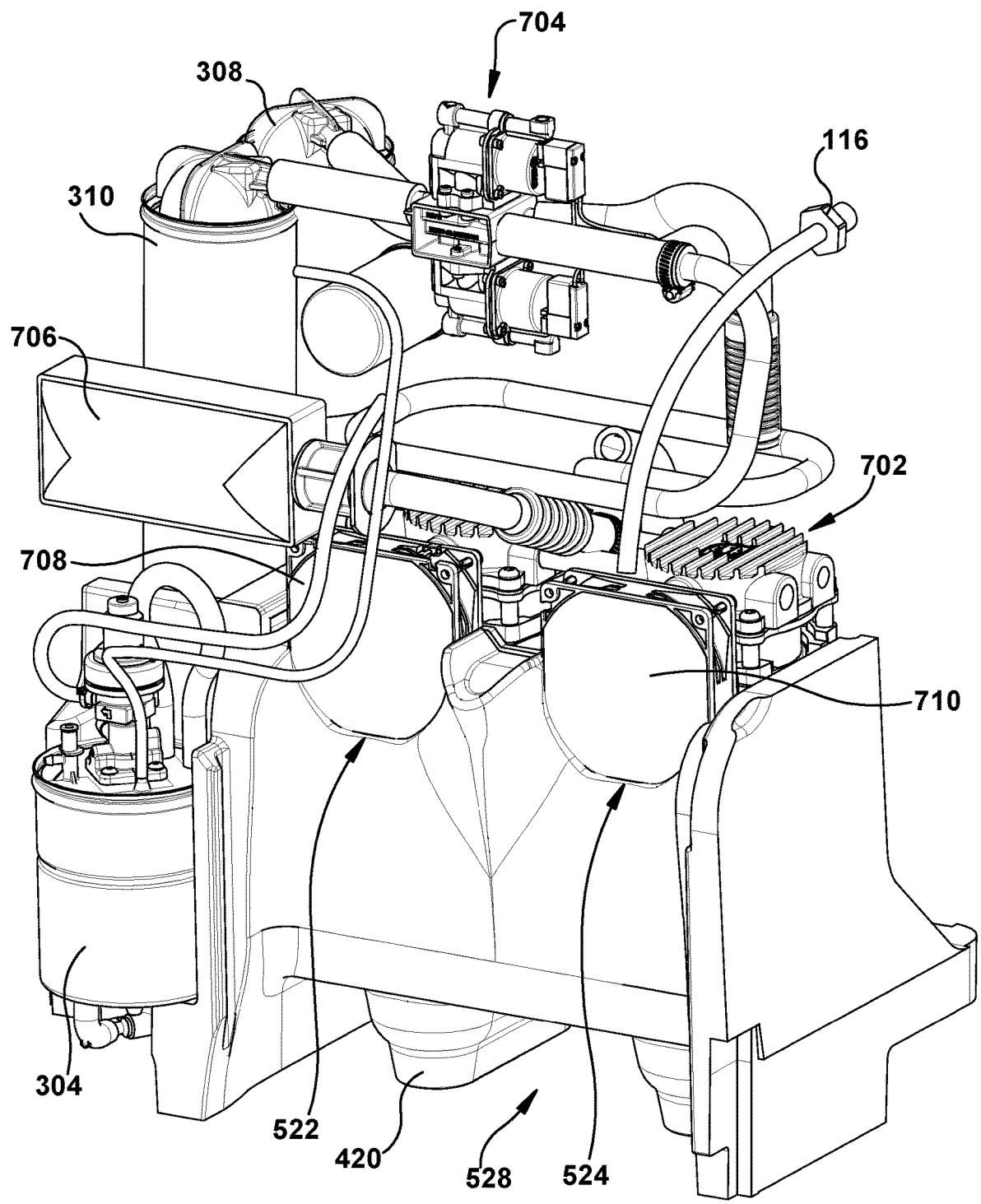
Figure 8D:
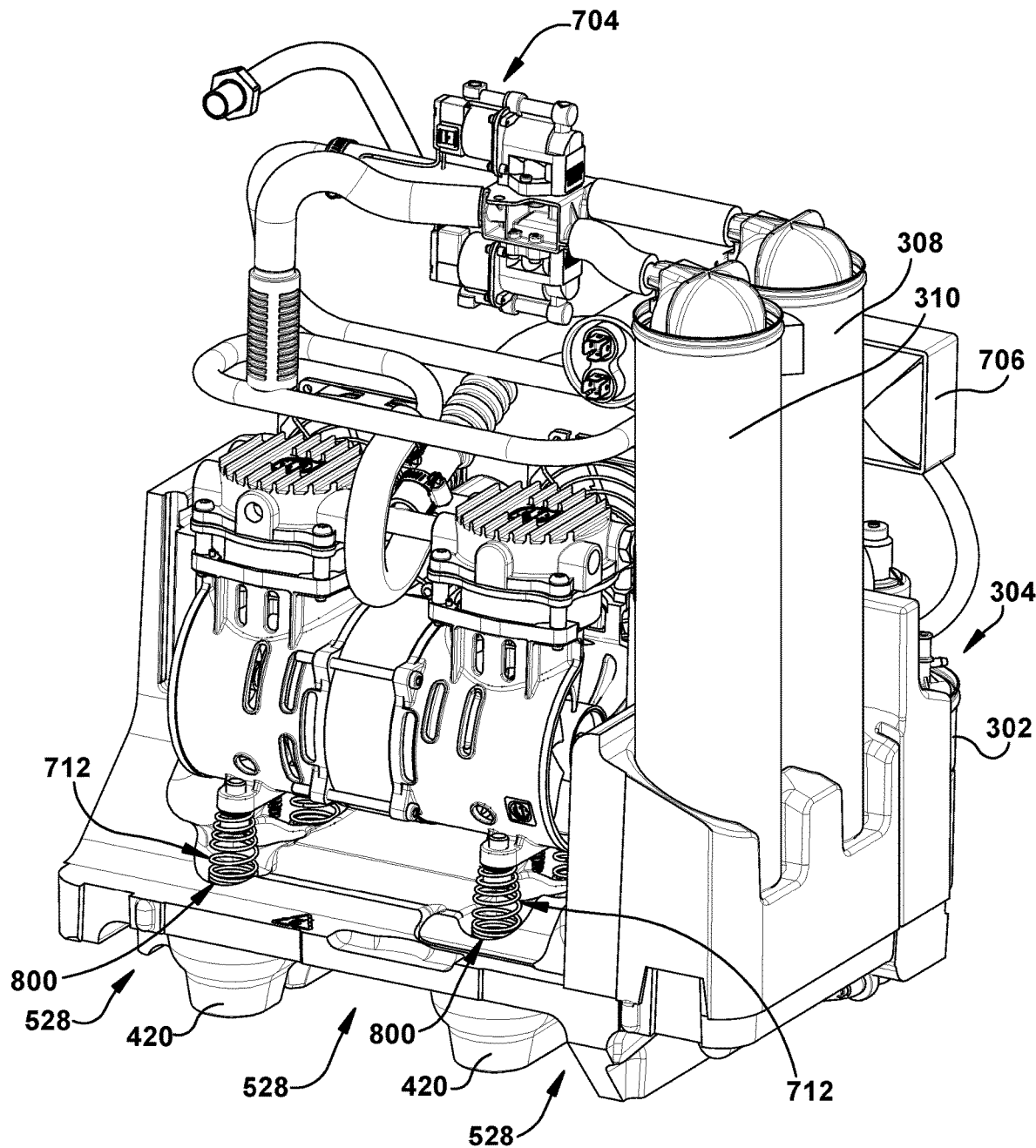

FIGS. 8C-8D are perspective views of the exemplary gas concentration system in association with bottom mounting body portion 508. In the embodiment shown, body portion 508 receives and retains a plurality of gas concentrating system components including, for example, compressor system 702, product tank 302, sieve beds 308 and 310. As previously described, these components are received and retained in spaces having surfaces arranged and configured for these components. As also previously described, these components are retained within mounting body 300 (and bottom portion 508) with or without the use of fasteners. In the embodiment illustrated, bottom mounting body portion 508 is arranged as a base structure for receiving and retaining the gas concentrating system components that are larger and heavier components (e.g., compressor system 702, sieve beds 308 and 310, and product tank 304). In other embodiments, the bottom mounting body portion 508 need not receive and retain all of these components. Some or all of these components can be received and retained in one or more other mounting body portions.

Figure 9A:
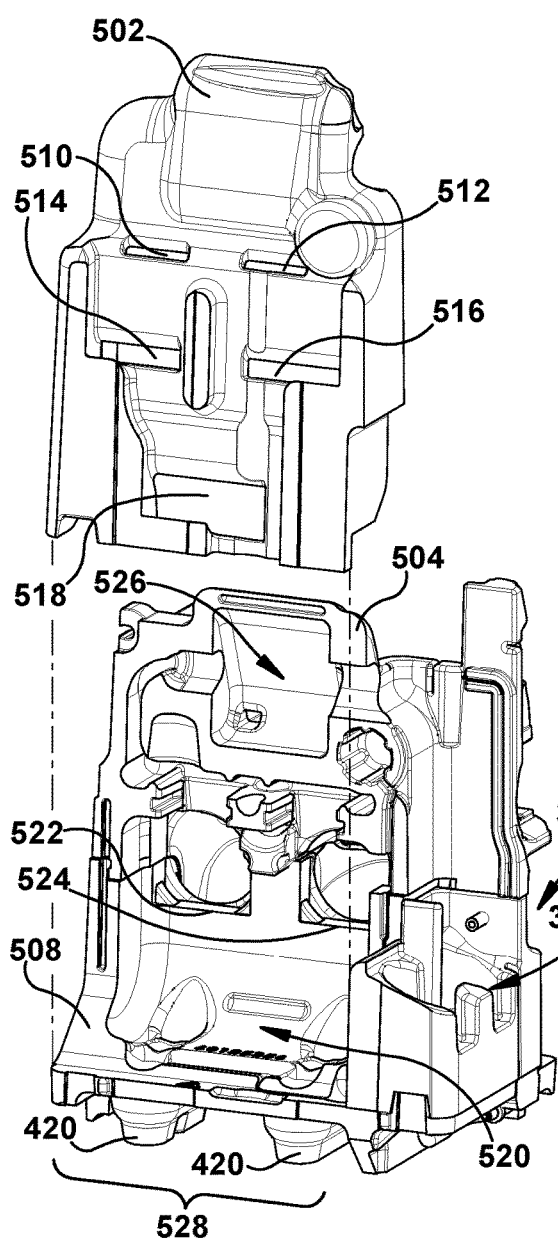
FIGS. 9A-9B are partial exploded views of one embodiment of a mounting body.
Figure 9B:
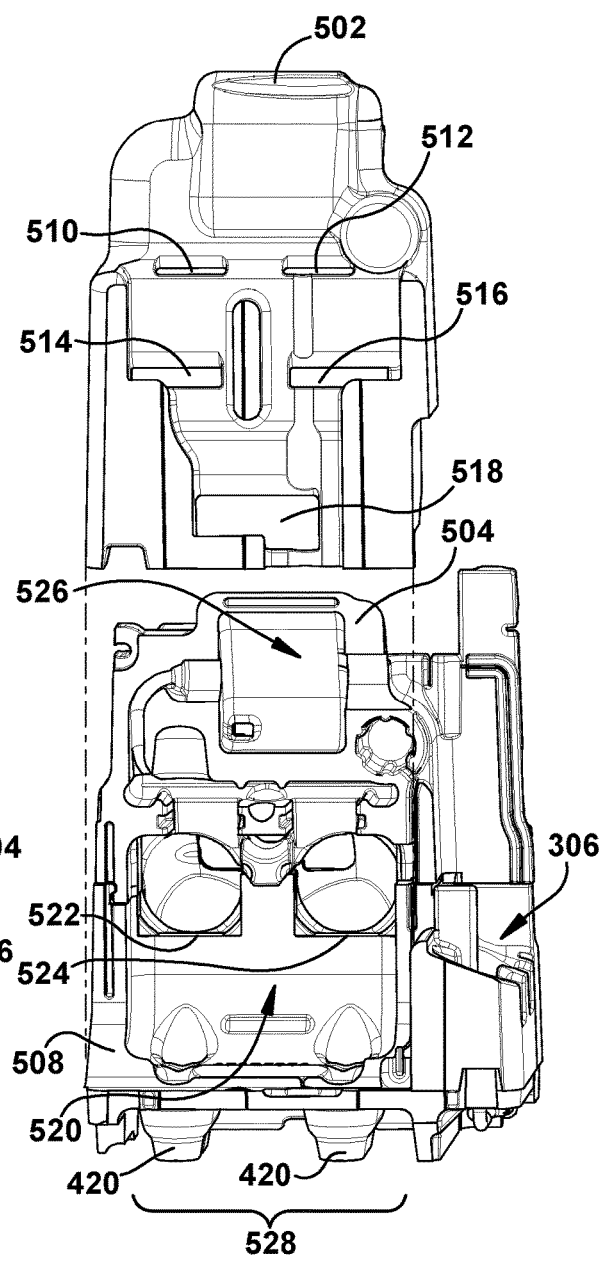

Referring now to FIGS. 9A-9B, back mounting body portion 502 is shown exploded away from mounting body portions 504 and 508. The location, size, and geometry of one embodiment of cooling air openings/intakes 510, 512, 514, 516, and 518 are illustrated. In this embodiment, upper cooling air openings 510 and 512 are axially spread apart and substantially elongate in nature. Middle cooling air openings 514 and 516 are similarly axially spread apart and also substantially elongate in nature. In the embodiment shown, the upper and middle cooling air openings are aligned with the spatial separation of the location of cooling fans 708 and 710. They are also aligned (axially) with the compressor system 702 heads and cooling fins (e.g., see 703) where heat is generated. In this manner, flow resistance is minimized when drawing cooling air into compressor space 520 and the location where the heat-generating components of the compressor system 702 are located. Cooling air opening 518 is located near the bottom of mounting body 300 and allows for cooling air to be introduced toward the bottom of the compressor space 520 and compressor system 702. This assists in cooling the electric motor of the compressor system 702. In other embodiments, the cooling air openings can have other locations and geometries.

Figure 10A:
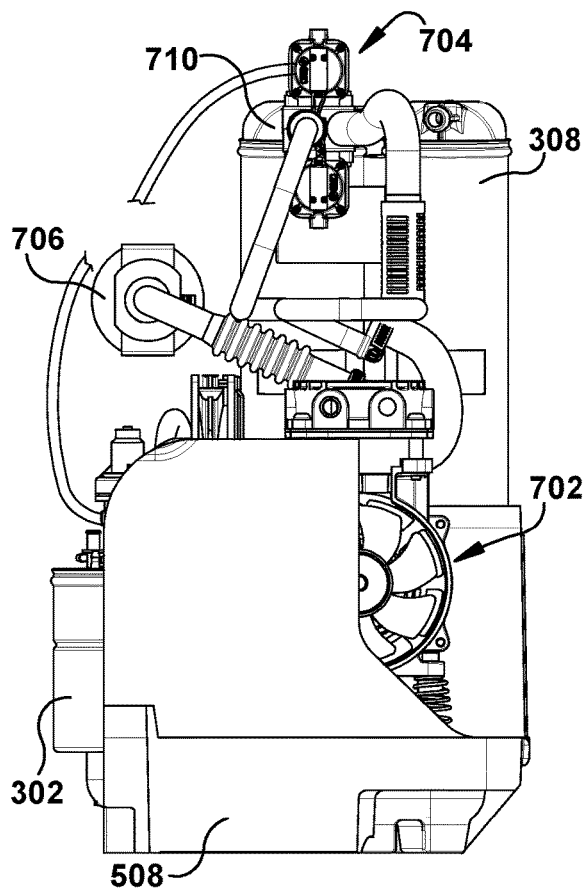
FIGS. 10A-10D or right, left, bottom, and top views of one portion of a mounting body and associated gas separation components.
Figure 10B:
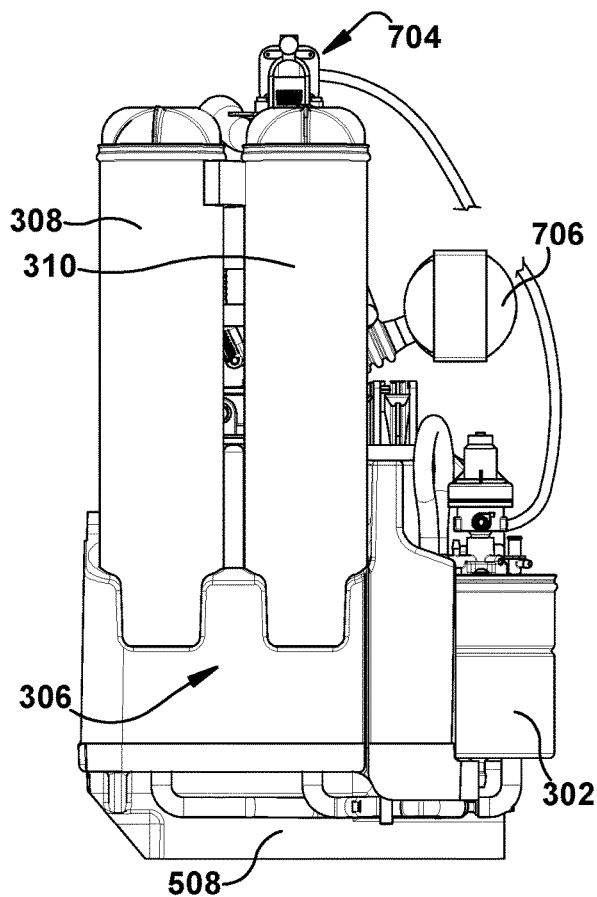
Figure 10C:
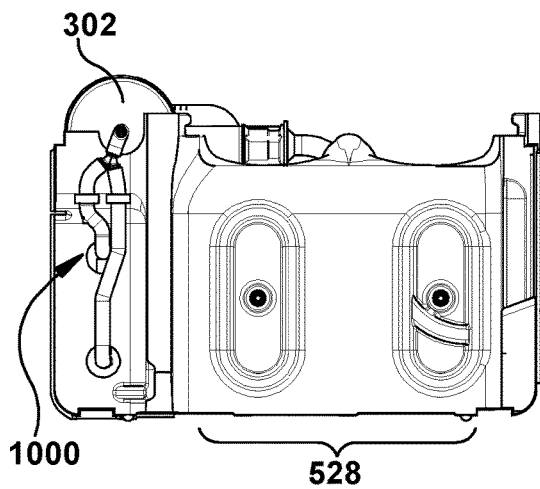
Figure 10D:
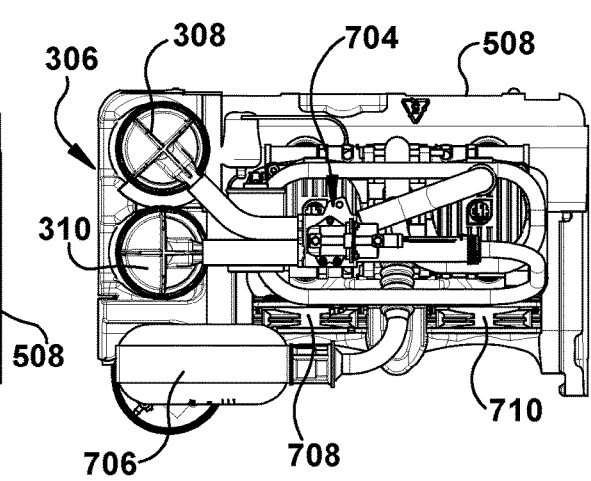

FIGS. 10A-10D illustrate various views of bottom mounting body portion 508 and its retention of various gas concentrating system components. As mentioned earlier, portion 508 can act as a base structure for the bulkier gas concentrating system components (e.g., compressor system 702, sieve beds 308 and 310, and product tank 304). FIGS. 10A-D also illustrate the various tubing of the gas concentrating system. For example, FIG. 10C is a bottom view of portion 508 showing the location of tubing 1000 that connects the sieve beds 308 and 310 to product tank 304.

Mounting body 300 can be made from various material including foam. In one embodiment, mounting body 300 is made from the closed cell foam material such as, for example, Expanded Polypropylene (EPP) foam. EPP foam provides energy absorption, impact resistance, thermal insulation, water and chemical resistance, and has a high strength to weight ratio and is recyclable. Arranged as shown and described herein, a gas concentrating system mounting body is provided that can receive and retain the gas concentrating system components with or without the use of fasteners. The use of fasteners is avoided by having mounting and retention spaces with surfaces that frictionally engage and retain (via a tight or friction, press, and/or interference fit connection) the surfaces of the components received therein. In other aspects, certain components can be retained within spaces that allow for component movement or vibration (e.g., compressor vibration) without transmitting the vibration to the walls of the mounting body while still securely retaining the component without the use of fasteners (e.g., via a tight or friction, press, and/or interference fit connection).

While the present inventions have been illustrated by the description of embodiments thereof, and while the embodiments have been described in considerable detail, it is not the intention of the descriptions to restrict or in any way limit the scope of the appended claims to such detail. Additional advantages and modifications will readily appear to those skilled in the art. Therefore, the inventions, in their broader aspects, are not limited to the specific details, the representative apparatus, and illustrative examples shown and described. Accordingly, departures can be made from such details without departing from the spirit or scope of the general inventive concepts.

What is claimed:

1. A method of operating a gas concentrating system comprising:
   providing cooling air into a compressor space through first and second spaced apart air inlets;
   generating a first air cooling path for cooling an external portion of a compressor head portion through the first inlet;
   generating a second air cooling path for cooling a compressor motor portion through second inlet;
   generating a third air cooling path for cooling a compressor output duct portion via a third air inlet; and
   exhausting the cooling air away from the compressor head and motor portions.

2. The method of claim 1, wherein generating a first air cooling path comprises directing cooling air across the compressor head portion.

3. The method of claim 1, wherein generating a second air cooling path comprises directing cooling air across the compressor motor portion.

4. The method of claim 1 wherein generating the first air cooling path for cooling the compressor head portion through the first inlet comprises generating the first air cooling path closer to the compressor head portion than the motor portion.

5. The method of claim 1 wherein generating the second air cooling path for cooling the compressor motor through the second inlet comprises generating the second air cooling path closer to the compressor motor portion than the head portion.

6. The method of claim 1 wherein generating the third air cooling path for cooling the compressor output duct portion via the third air inlet comprises generating the third air cooling path closer to the compressor output duct portion than the head portion.

7. The method of claim 1 wherein exhausting the cooling air away from the compressor head and motor portions comprises directing the air along an exhaust path that is insulated from the compressor space.

8. The method of claim 1 wherein exhausting the cooling air away from the compressor head and motor portion comprises directing the cooling air along an exhaust path exiting away from a front portion of the gas concentrating system.

9. The method of claim 1 wherein exhausting the cooling air away from the compressor head and motor portion comprises directing the cooling air along an insulated exhaust path exiting away from a top portion of the gas concentrating system.

10. A method of cooling a gas concentrating system comprising:
providing a cooling airstream from at least one air intake;
directing at least a first portion of the cooling airstream into at least a first inlet of a compressor space and to an external portion of a head portion of a compressor;
directing at least a second portion of the cooling airstream into at least a second inlet of the compressor space and to a motor portion of the compressor;
directing at least a third portion of the cooling airstream into at least a third inlet of the compressor space and to a compressor output duct space; and
exhausting the first and second portions of the cooling airstream away from the head and motor portions of the compressor.

11. The method of claim 10 wherein exhausting the first and second portions of the airstream away from the head and motor portions of the compressor comprises directing the airstream along an exhaust path that is insulated from the compressor space.

12. The method of claim 10 wherein directing the third portion of the airstream into the compressor output duct space comprises directing the third portion of the cooling airstream into a compressor duct space that is isolated from the compressor space.

13. A method of cooling a gas concentrating system comprising:
providing an internal mounting body and an external housing;
providing an airstream from at least one air intake and into first and second passageways between the internal mounting body and external housing;
directing a portion of the airstream in the first passageway into at least a first inlet of the mounting body and into the second passageway;
directing another portion of the airstream in the second passageway into at least a second inlet of the mounting body;
directing portions of the airstream in the second passageway into at least a third passageway and a third inlet of the mounting body; and
exhausting portions of the airstream from the mounting body.

14. The method of claim 13 wherein directing the portion of the airstream in the first passageway into at least the first inlet of the mounting body comprises directing the portion of the airstream in the first passageway closer to a head portion of a compressor than a motor portion.

15. The method of claim 13 wherein directing the portion of the airstream in the second passageway into at least the second inlet of the mounting body comprises directing the portion of the airstream in the second passageway closer to a motor portion of a compressor than a head portion.

16. The method of claim 13 wherein directing portions of the airstream in the second passageway into at least the third passageway and the third inlet of the mounting body comprises directing portions of the airstream from the third inlet to at least one output duct of a compressor.

17. The method of claim 13 further comprising directing portions of the airstream entering the third inlet into an output duct space that is insulated from a compressor space.

* * * * *